US012642863B2

(12) United States Patent
Sato et al.

(10) Patent No.: US 12,642,863 B2
(45) Date of Patent: Jun. 2, 2026

(54) CONJUGATE AND PHOTOIMMUNOTHERAPY

(71) Applicants: JSR CORPORATION, Minato-ku (JP); NATIONAL UNIVERSITY CORPORATION TOKAI NATIONAL HIGHER EDUCATION AND RESEARCH SYSTEM, Nagoya (JP)

(72) Inventors: Kazuhide Sato, Nagoya (JP); Hiroshi Yukawa, Nagoya (JP); Kohei Matsuoka, Nagoya (JP); Yuuichi Ueya, Minato-ku (JP); Mibuko Shimada, Minato-ku (JP); Kenichiro Ono, Minato-ku (JP)

(73) Assignees: JSR CORPORATION, Minato-ku (JP); NATIONAL UNIVERSITY CORPORATION TOKAI NATIONAL HIGHER EDUCATION AND RESEARCH SYSTEM, Nagoya (JP)

( * ) Notice: Subject to any disclaimer, the term of this patent is extended or adjusted under 35 U.S.C. 154(b) by 556 days.

(21) Appl. No.: 18/044,728

(22) PCT Filed: Sep. 7, 2021

(86) PCT No.: PCT/JP2021/032856

§ 371 (c)(1),
(2) Date: Mar. 9, 2023

(87) PCT Pub. No.: WO2022/054798

PCT Pub. Date: Mar. 17, 2022

(65) Prior Publication Data

US 2023/0330252 A1 Oct. 19, 2023

(30) Foreign Application Priority Data

Sep. 11, 2020 (JP) ................................ 2020-153246

(51) Int. Cl.

| | |
|---|---|
| ***A61K 47/68*** | (2017.01) |
| ***A61K 41/00*** | (2020.01) |
| ***A61K 49/18*** | (2006.01) |
| ***B82Y 5/00*** | (2011.01) |
| ***B82Y 30/00*** | (2011.01) |

(52) U.S. Cl.

CPC ...... *A61K 47/6849* (2017.08); *A61K 41/0052* (2013.01); *A61K 49/1875* (2013.01); *B82Y 5/00* (2013.01); *B82Y 30/00* (2013.01)

(58) Field of Classification Search

None

See application file for complete search history.

(56) References Cited

U.S. PATENT DOCUMENTS

| | | | |
|---|---|---|---|
| 2014/0284528 | A1 | 9/2014 | Yukawa et al. |
| 2016/0015829 | A1 | 1/2016 | Kobayashi et al. |
| 2021/0401986 | A1 | 12/2021 | Makings et al. |

FOREIGN PATENT DOCUMENTS

| | | | |
|---|---|---|---|
| JP | 2014-523907 | A | 9/2014 |
| JP | 2014-185224 | A | 10/2014 |
| JP | 2019-218374 | A | 12/2019 |
| WO | WO 2009/038659 | A2 | 3/2009 |
| WO | WO 2017/031367 | A1 | 2/2017 |
| WO | WO 2020/210712 | A2 | 10/2020 |

OTHER PUBLICATIONS

Sato et al (ACS Cent. Sci., 4:1559-1569, 2018).*
Tseng et al (Int. J. Nanomed., 10:3663-3685, 2015).*
Lee et al (Bioconjugate Chem. 21:940-946, 2010.*
International Search Report issued Nov. 30, 2021, in PCT/JP2021/032856, filed on Sep. 7, 2021, 3 pages.
Sato, "A Mechanism of Cancer Cell Cytotoxicity of Near-Infrared Photoimmunotherapy", The Journal of Japan Society for Laser Surgery and Medicine, Jul. 2020, vol. 41, No. 2, pp. 104-109 (with English Abstract).
Kobayashi et al., "Near-infrared photoimmunotherapy of cancer: a new approach that kills cancer cells and enhances anti-cancer host immunity", International Immunology, Jun. 2020, vol. 33, No. 1, pp. 7-15.
Tseng et al., "Cetuximab-conjugated iron oxide nanoparticles for cancer imaging and therapy", Int. J. Nanomedicine, 2015, vol. 10, No. 1, pp. 3663-3685.
Lin et al., "Bevacizumab and Near Infrared Probe Conjugated Iron Oxide Nanoparticles for Vascular Endothelial Growth Factor Targeted MR and Optical Imaging", Biomater Sci., 2018, vol. 6, No. 6, pp. 1517-1525.

(Continued)

*Primary Examiner* — Brian Gangle
(74) *Attorney, Agent, or Firm* — Oblon, McClelland, Maier & Neustadt, L.L.P.

(57) ABSTRACT

Provided is a drug useful for photoimmunotherapy. Specifically, provided is a conjugate including an antibody molecule, a particle having an average particle diameter of 100 nm or less, and a photosensitive portion. In the conjugate, the particle having an average particle diameter of 100 nm or less is linked to the antibody molecule, and at least one of the antibody molecule or the particle is bound to the photosensitive portion. The photosensitive portion is a portion showing increase of hydrophobicity when irradiated with a light beam having a wavelength of from 500 nm to 900 nm or a portion containing a phthalocyanine skeleton.

17 Claims, 5 Drawing Sheets

(56) References Cited

OTHER PUBLICATIONS

Wang et al., "In vivo MR and Fluorescence Dual-modality Imaging of Atherosclerosis Characteristics in Mic Using Profilin-1 Targeted Magnetic Nanoparticles", Theranostics, 2016, vol. 6, Issue 2, pp. 272-286.

Kobayashi et al., "Super-enhanced permeability and retention (SUPR) effect induced by photo-immunotherapy (PIT) can accommodate massive nano-sized reagents deep into tumors", Cancer Research, 2013, vol. 73, No. 8 (suppl.), Proceedings: AACR 104th Annual Meeting 2013 Abstract 4512, 3 pages.

Extended European Search Report issued Jan. 2, 2026 in European Patent Application No. 21866757.4, 17 pages.

Pille et al., "Self-Assembling VHH-Elastin-Like Peptides for Photodynamic Nanomedicine", BioMacromolecules, Mar. 7, 2017, pp. 1302-1310, XP 055815275.

Stuchinskaya et al., "Targeted Photodynamic Therapy of Breast Cancer Cells Using antibody-phthalocyanine-gold nanoparticle conjugates", Photochemical & Photobiological Sciences, vol. 10, No. 5, Apr. 1, 2011, pp. 822-831 (Total 11 pages).

* cited by examiner

CONJUGATE AND PHOTOIMMUNOTHERAPY

CROSS REFERENCE TO RELATED APPLICATIONS

This application is a National Stage entry under 35 U.S.C. § 371 of PCT/JP2021/032856, filed on Sep. 7, 2021, and claims priority to Japanese Patent Application No. 2020-153246, filed on Sep. 11, 2020, the entire contents of which are incorporated herein by reference.

TECHNICAL FIELD

The present invention relates to a conjugate and a photoimmunotherapy using the same.

BACKGROUND ART

As an innovative cancer treatment method, near-infrared photoimmunotherapy (NIR-PIT) has been attracting attention (see, for example, Patent Literatures 1 and 2 and Non Patent Literature 1). NIR-PIT is a treatment method involving: preparing an antibody conjugate, which is obtained by introducing a photosensitive substance that reacts to a near-infrared ray into an antibody specific for an antigen on a tumor cell surface; allowing the antibody conjugate to bind to tumor cells; and locally radiating a near-infrared ray, to thereby selectively kill the tumor cells. A chemical species containing a phthalocyanine skeleton (e.g., a so-called IR700 molecule such as IRDye700DX) has been mainly used as the photosensitive substance. NIR-PIT is excellent in terms of high light-transmitting property and low invasiveness for a patient's body. Meanwhile, there are demands for further improvements in killing effect on tumor cells in NIR-PIT and imaging performance.

Hitherto, it has been considered that the mechanism of cell death caused by the photosensitive substance is mainly oxidative stress due to a free radical or the like. Meanwhile, the detailed mechanism of the killing of tumor cells by NIR-PIT has not been clear. However, it has recently been elucidated that the mechanism of the tumor therapeutic effect of NIR-PIT is as follows: the photosensitive substance of the antibody conjugate bound to the tumor cell surface becomes hydrophobic through a photochemical reaction to cause aggregation of the antibody conjugate, thereby disrupting cell membranes of the tumor cells, and as a result, a difference in osmotic pressure between the inside and outside of the cells occurs to induce cell death (Non Patent Literature 1).

In the fields of medicine and biology, imaging is an important technology applied to, for example, generation of a medical image, and a biosensor. In recent years, imaging using quantum dots has been attracting attention by virtue of combining advantages, such as a high emission quantum yield, a wide absorption region, and resistance to bleaching. In Patent Literature 3, there are descriptions of: a semiconductor nanoparticle having a core-shell structure that includes a core and a shell surrounding the core, wherein the core is made of $(AgIn)_xZn_{2(1-x)}S_2$ ("x" satisfies $0.4 \leq x \leq 0.95$), wherein the shell is made of ZnS or ZnO, and wherein the semiconductor nanoparticle has a hydrophilic functional group on a surface of the shell; and a fluorescent probe for biological sample labeling using the semiconductor nanoparticle.

CITATION LIST

Patent Literature

[PTL 1] JP 2014-523907 A
[PTL 2] JP 2019-218374 A
[PTL 3] JP 2014-185224 A

Non Patent Literature

[NPL 1] The 40th Annual Meeting of Japan Society for Laser Surgery and Medicine Prize-Winning Article "A Mechanism of Cancer Cell Cytotoxicity of Near-Infrared Photoimmunotherapy", The Journal of Japan Society for Laser Surgery and Medicine, 2020, Vol. 41, No. 2, p. 104-109

SUMMARY OF INVENTION

Technical Problem

The present invention provides a drug for photoimmunotherapy (PIT), which is improved in killing effect on tumor cells and imaging performance, and a method of treating a tumor by PIT using the drug.

Solution to Problem

The inventors of the present invention found that a conjugate comprising an antibody molecule and a photosensitive substance and further comprising a particle having an average particle diameter of 100 nm or less is excellent in imaging of a tumor and therapeutic effect of PIT.

Accordingly, the present invention provides the following.

[1] A conjugate, comprising: an antibody molecule; and a particle having an average particle diameter of 100 nm or less, which is linked to the antibody molecule, wherein at least one of the antibody molecule or the particle is bound to a portion showing increase of hydrophobicity when irradiated with a light beam having a wavelength of from 500 nm to 900 nm.

[2] A conjugate, comprising: an antibody molecule; and a particle having an average particle diameter of 100 nm or less, which is linked to the antibody molecule, wherein at least one of the antibody molecule or the particle is bound to a portion containing a phthalocyanine skeleton. (The above-mentioned "portion showing increase of hydrophobicity when irradiated with a light beam having a wavelength of from 500 nm to 900 nm" and "portion containing a phthalocyanine skeleton" are hereinafter sometimes collectively referred to as "photosensitive portion".)

[3] The conjugate according to Embodiment [1] or [2], wherein the particle is a magnetic particle or a semiconductor particle.

[4] The conjugate according to Embodiment [1] or [3], wherein the antibody molecule is bound to the portion showing increase of hydrophobicity when irradiated with a light beam having a wavelength of from 500 nm to 900 nm.

[5] The conjugate according to Embodiment [2] or [3], wherein the antibody molecule is bound to the portion containing a phthalocyanine skeleton.

[6] The conjugate according to Embodiment [2], [3], or [5], wherein the portion containing a phthalocyanine skeleton is a compound represented by the following formula (Ia):

(Ia)

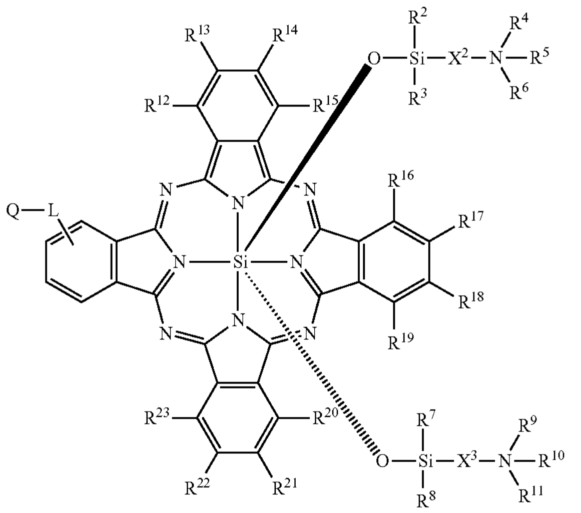

where:

L represents a direct bond or a linker;

Q represents a reactive group for forming a bond to the antibody molecule or the particle;

$R^2$, $R^3$, $R^7$, and $R^8$ are each independently selected from a substituted or unsubstituted alkyl and a substituted or unsubstituted aryl;

$R^4$, $R^5$, $R^6$, $R^9$, $R^{10}$, and $R^{11}$, when present, are each independently selected from hydrogen, a substituted or unsubstituted alkyl, a substituted or unsubstituted alkanoyl, a substituted or unsubstituted alkoxycarbonyl, a substituted or unsubstituted alkylcarbamoyl, and a chelating ligand, wherein at least one of $R^4$, $R^5$, $R^6$, $R^9$, $R^{10}$, or $R^{11}$ contains a water-soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are each independently selected from hydrogen, a halogen, a substituted or unsubstituted alkylthio, a substituted or unsubstituted alkylamino, and a substituted or unsubstituted alkoxy, or at least one of i) $R^{13}$ and $R^{14}$, and carbon atoms to which $R^{13}$ and $R^{14}$ are bonded, ii) $R^{17}$ and $R^{18}$, and carbon atoms to which $R^{17}$ and $R^{18}$ are bonded, or iii) $R^{21}$ and $R^{22}$, and carbon atoms to which $R^{21}$ and $R^{22}$ are bonded, form a fused ring; and $X^2$ and $X^3$ each independently represent a $C_1$ to $C_{10}$ alkylene with or without an intervening heteroatom between carbon-carbon bonds.

[7] The conjugate according to Embodiment [6], wherein the compound represented by the formula (Ia) is a compound represented by the following formula (Ib):

(Ib)

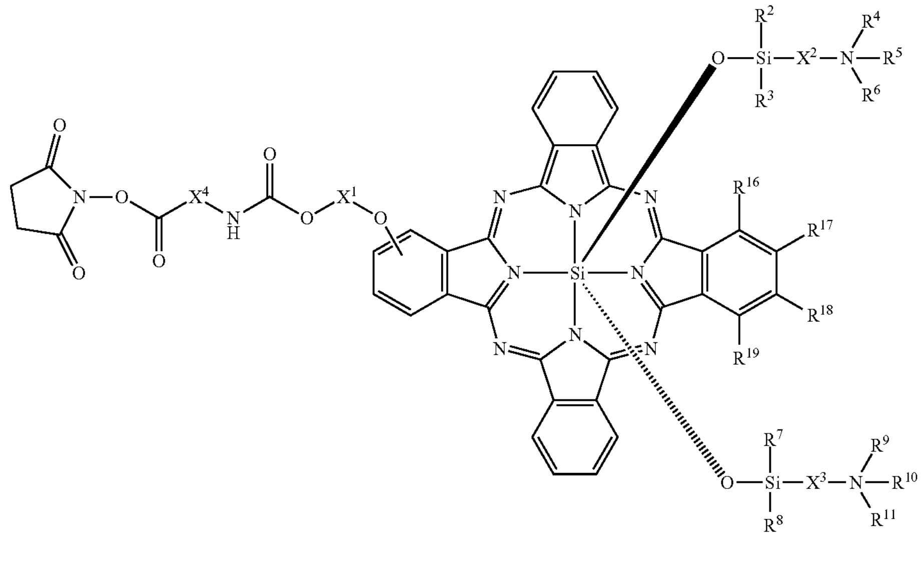

where:

$X^1$ and $X^4$ each independently represent a $C_1$ to $C_{10}$ alkylene with or without an intervening heteroatom; and $R^2$, $R^3$, $R^4$, $R^5$, $R^6$, $R^7$, $R^8$, $R^9$, $R^{10}$, $R^{11}$, $R^{16}$, $R^{17}$, $R^{18}$, $R^{19}$, $X^2$, and $X^3$ are as defined in Embodiment [6].

[8] The conjugate according to Embodiment [6], wherein the compound represented by the formula (Ia) is a compound represented by the following formula (II).

(II)

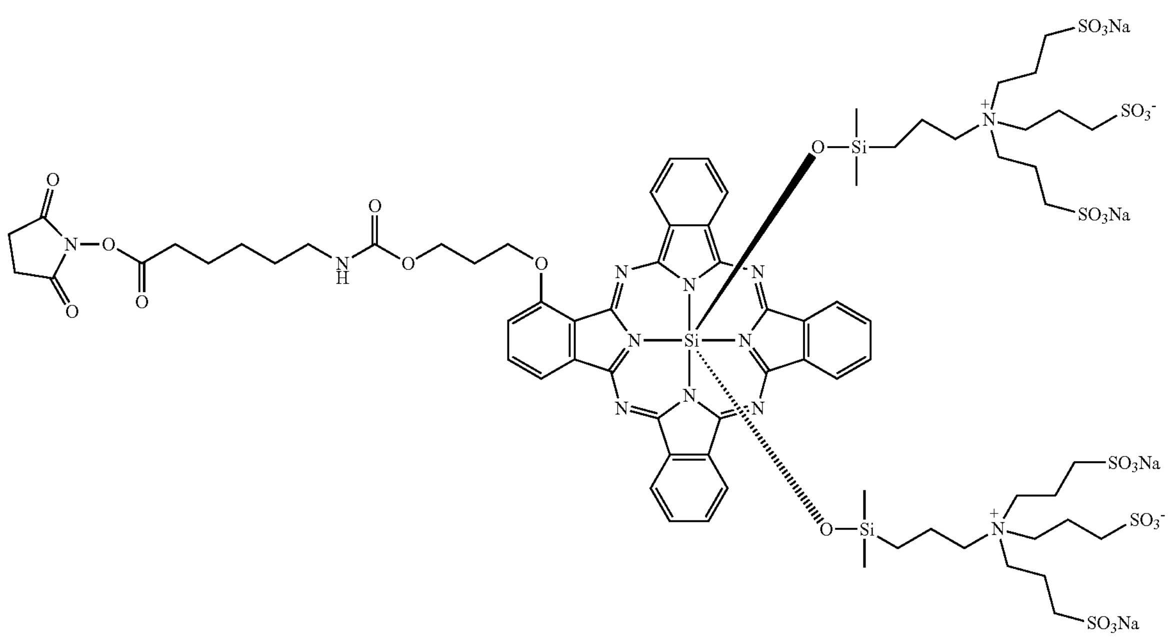

[9] The conjugate according to any one of Embodiments [3] to [8], wherein the magnetic particle contains iron oxide or a gadolinium compound.

[10] The conjugate according to any one of Embodiments [3] to [8], wherein the semiconductor particle is a quantum dot.

[11] The conjugate according to any one of Embodiments [1] to [10], wherein the average particle diameter of the particle is from 1 nm to 50 nm.

[12] The conjugate according to any one of Embodiments [1] to [11], wherein a number of the antibody molecules linked to the particle is from 1 to 20 per the particle.

[13] A composition, comprising the conjugate of any one of Embodiments [1] to [12].

[14] The conjugate according to any one of Embodiments [1] to [12], wherein the conjugate is for use in treatment of a tumor by photoimmunotherapy.

[15] The conjugate according to Embodiment [14], wherein the conjugate is further for use in imaging of a tumor.

[16] The composition according to Embodiment [13], wherein the composition is for use in treatment of a tumor by photoimmunotherapy.

[17] The composition according to Embodiment [16], wherein the composition is further for use in imaging of a tumor.

[18] A use of the conjugate of any one of Embodiments [1] to [12] in production of a tumor therapeutic agent for photoimmunotherapy.

[19] The use of the conjugate according to Embodiment [18], wherein the tumor therapeutic agent is further used for imaging of a tumor.

[20] A method of treating a tumor, comprising the steps of:

administering the conjugate of any one of Embodiments [1] to [12] or the composition of Embodiment [13] to a patient; and irradiating the patient with a light beam having a wavelength of from 500 nm to 900 nm.

[21] The method according to Embodiment [20], further comprising, before the step of irradiating the patient with the light beam, a step of imaging a tumor of the patient having administered thereto the conjugate or the composition.

[22] A tumor therapeutic agent for photoimmunotherapy, comprising the conjugate of any one of Embodiments [1] to [12].

[23] The tumor therapeutic agent according to Embodiment [22], wherein the tumor therapeutic agent is an agent for imaging of a tumor and tumor treatment by photoimmunotherapy.

Advantageous Effects of Invention

The conjugate of the present invention has a high killing effect on tumor cells and high imaging performance, and can improve the therapeutic effect of PIT on a tumor.

DESCRIPTION OF EMBODIMENTS

Figure 1:
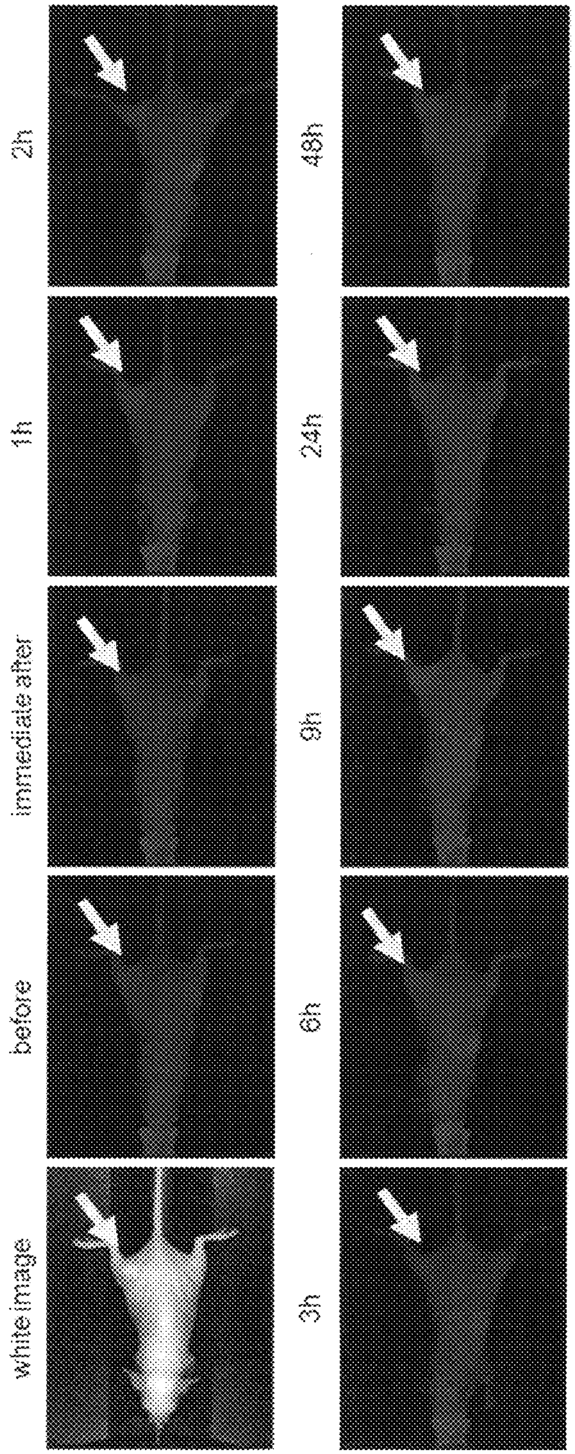
FIG. 1 shows fluorescence imaging of a tumor cell-implanted mouse administered Nanomag-Pan-IR700. Fluorescence images of the whole body of the mouse from before the administration (before) to 48 hours after the administration (48 h) are shown. Arrows each indicate the injection site of tumor cells.

All patent literatures, non patent literatures, and other publications cited herein are incorporated herein by reference in their entirety.

As used herein, the term "tumor" refers to tumors in general including benign and malignant tumors, and epithelial and nonepithelial tumors, and sites of occurrence thereof (tissues and organs) are also not particularly limited. A tumor to be targeted in the present invention is preferably a malignant tumor such as cancer. The cancer may be a liquid tumor or a solid tumor, and may encompass all kinds of cancers, such as epithelial cancer, adenocarcinoma, sarcoma, and malignant lymphoma. Examples of the tumor include: liquid tumors, including acute leukemia (e.g., acute lymphocytic leukemia, acute myelogenous leukemia, myeloblastic leukemia, promyelocytic leukemia, myelomonocytic leukemia, monocytic leukemia, and erythroleukemia), chronic leukemia (e.g., chronic myelogenous (granulocytic) leukemia, chronic lymphocytic leukemia, and hairy cell leukemia), T-cell prolymphocytic leukemia, large granular lymphocytic leukemia, adult T-cell leukemia, polycythemia vera, Hodgkin lymphoma, non-Hodgkin lymphoma, multiple myeloma, Waldenstrom macroglobulinemia, heavy chain disease, and the like; and solid tumors, including fibrosarcoma, myxosarcoma, liposarcoma, chondrosarcoma, osteogenic sarcoma, other sarcomas, synovioma, mesothelioma, Ewing's tumor, leiomyosarcoma, rhabdomyosarcoma, colon cancer, pancreatic cancer, breast cancer, ovarian cancer, prostate cancer, hepatocellular carcinoma, lung cancer, colorectal cancer, squamous cell carcinoma, basal cell carcinoma, adenocarcinoma (e.g., adenocarcinoma of the pancreas, colon, ovary, lung, breast, stomach, prostate, uterine cervix, or esophagus), sweat gland cancer, sebaceous adenocarcinoma, papillary cancer, papillary adenocarcinoma, medullary cancer, bronchogenic cancer, renal cell carcinoma, hepatoma, bile duct cancer, choriocarcinoma, Wilms tumor, cervical cancer, testicular tumor, bladder cancer, glioma, astrocytoma, medulloblastoma, craniopharyngioma, ependymoma, pinealoma, hemangioblastoma, acoustic neurinoma, oligodendroglioma, meningioma, melanoma, neuroblastoma, retinoblastoma, and the like. Herein, the tumor may be a primary tumor or a recurrent tumor.

As used herein, the term "tumor-affected area" or "affected area" refers to a tumor tissue in which tumor cells are mainly present. The tumor tissue encompasses a tissue formed of tumor cells and a tissue in which tumor cells are mixed with normal cells or a normal tissue. When the tumor tissue has normal cells or a normal tissue mixed therein, the ratio of the volume or cell count of the tumor cells to the normal cells or the normal tissue is not particularly limited.

The term "antibody" as used herein refers to a polypeptide ligand containing at least one light chain variable region and/or heavy chain variable region that specifically recognizes an epitope of an antigen and binds thereto. For example, the term "antibody" as used herein encompasses immunoglobulins of any classes, such as IgG, IgA, IgD, IgE, IgM, and subclasses thereof, and variants thereof, and further encompasses a chimeric antibody such as a humanized antibody, any other immunoglobulin modification product containing an antigen recognition site, and the like. In addition, the "antibody" herein contains a fragment or domain of an immunoglobulin containing an antigen recognition site, such as a Fab fragment, a Fab' fragment, an F(ab)'2 fragment, a single-chain Fv ("scFv"), a disulfide-stabilized Fv ("dsFv"), a VHH (variable domain of heavy chain of heavy chain antibody), or a VNAR (single variable new antigen receptor domain antibody).

1. Conjugate

In one aspect, the present invention provides a conjugate to be used as a drug for photoimmunotherapy (PIT). The conjugate provided by the present invention comprises an antibody molecule, a particle having an average particle diameter of 100 nm or less (hereinafter sometimes referred to as "core particle"), and a photosensitive portion. In the conjugate, the core particle is linked to the antibody molecule, and at least one of the antibody molecule or the particle is linked to the photosensitive portion.

1.1. Antibody Molecule

The antibody molecule contained in the conjugate of the present invention is a molecule of an antibody that binds to a target tumor cell. The kind of the antibody may be appropriately selected in accordance with an antigen present on the surface of the target tumor cell. Examples of the antigen include a protein, a lipid, a polysaccharide, and a nucleic acid, and a preferred example thereof is a cell surface protein present on the surface of the target tumor cell.

An example of the cell surface protein is a tumor-specific protein expressed on the surface of the tumor cell (also known as "tumor-specific antigen" in the art). The tumor-specific protein is a protein that is unique to cancer cells, or that is more abundant in cancer cells than in other cells such as normal cells.

Examples of the tumor-specific protein include members of the epidermal growth factor receptor (EGFR) family (e.g., HER1, 2, 3, and 4), and cytokine receptor members (e.g., CD20, CD25, IL-13R, CD5, and CD52). For example, HER2 is mainly found in breast cancer, and HER1 is mainly found in adenocarcinoma, which is found in many organs, such as the pancreas, breast, prostate, and colon.

Specific examples of the tumor-specific protein include: human epidermal growth factor receptor 2 (HER-2, e.g., GenBank accession numbers M16789.1, M16790.1, M16791.1, M16792.1, and AAA58637), which is associated with breast cancer, ovarian cancer, stomach cancer, and uterine cancer; and HER-1 (e.g., GenBank accession numbers NM_005228 and NP_005219), which is associated with lung cancer, anal cancer, and glioma as well as adenocarcinoma.

Other specific examples of the tumor-specific protein include: CD52 (e.g., GenBank accession numbers AAH27495.1 and CAI15846.1), which is associated with chronic lymphocytic leukemia; CD33 (e.g., GenBank accession numbers NM_023068 and CAD36509.1), which is associated with acute myelogenous leukemia; and CD20 (e.g., GenBank accession numbers NP_068769 and NP_031667), which is associated with non-Hodgkin lymphoma.

Other specific examples of the tumor-specific protein include: any of various MAGEs (melanoma-associated antigen E) including MAGE1 (e.g., GenBank accession numbers M77481 and AAA03229), MAGE2 (e.g., GenBank accession numbers L18920 and AAA17729), MAGE3 (e.g., GenBank accession numbers U03735 and AAA17446), MAGE4 (e.g., GenBank accession numbers D32075 and A06841.1), and the like; any of various tyrosinases (e.g., GenBank accession numbers U01873 and AAB60319); mutant ras; mutant p53 (e.g., GenBank accession numbers X54156, CAA38095, and AA494311); p97 melanoma antigen (e.g., GenBank accession numbers M12154 and AAA59992); human milk fat globule (HMFG) (e.g., GenBank accession numbers 556151 and AAB19771), which is associated with breast tumor; any of various BAGEs (human B-melanoma-associated antigen E) including BAGE1 (e.g., GenBank accession number Q13072) and BAGE2 (e.g., GenBank accession numbers NM_182482 and NP_872288); gp100 (e.g., GenBank accession numbers S73003 and AAC60634), which is associated with melanoma; MART1 antigen (e.g., GenBank accession number NP_005502), which is associated with melanoma; any of various GAGEs (G antigen) including GAGE1 (e.g., GenBank accession number Q13065) or any of GAGE2 to GAGE6; various gangliosides; and CD25 (e.g., GenBank accession numbers NP_000408.1 and NM_000417.2).

Other specific examples of the tumor-specific protein include HPV16/18 and E6/E7 antigens (e.g., GenBank accession numbers NC_001526, FJ952142.1, ADB94605, ADB94606, and U89349), which are associated with cervical cancer; mucin (MUC1)-KLH antigen (e.g., GenBank accession numbers J03651 and AAA35756), which is associated with breast cancer; carcinoembryonic antigen (CEA) (e.g., GenBank accession numbers X98311 and CAA66955), which is associated with colorectal cancer; and cancer antigen 125 (CA125 or also known as mucin 16 or MUC16) (e.g., GenBank accession numbers NM_024690 and NP_078966), which is associated with ovarian cancer and any other cancer; alpha-fetoprotein (AFP) (e.g., GenBank accession numbers NM_001134 and NP_001125), which is associated with liver cancer; Lewis Y antigen, which is associated with colorectal cancer, biliary tract cancer, breast cancer, small cell lung cancer, and any other cancer; tumor-associated glycoprotein 72 (TAG72), which is associated with adenocarcinoma; and PSA antigen (e.g., GenBank accession numbers X14810 and CAA32915), which is associated with prostate cancer.

Other specific examples of the tumor-specific protein include: prostate membrane specific antigen (PMSA; e.g., GenBank accession numbers AAA60209 and AAB81971.1), which is associated with prostate cancer; NY-ESO-1 (e.g., GenBank accession numbers U87459 and AAB49693), which is associated with melanoma, sarcoma, testicular cancer, and any other cancer; hTERT (alias: telomerase) (e.g., GenBank accession numbers NM_198253 and NP_937983 (variant 1), and NM_198255 and NP_937986 (variant 2)); proteinase 3 (e.g., GenBank accession numbers M29142, M75154, M96839, X55668, NM00277, M96628, X56606, CAA39943, and AAA36342); and Wilms' tumor 1 (WT-1, e.g., GenBank accession numbers NM_000378 and NP_000369 (variant A), NM_024424 and NP_077742 (variant B), NM_024425 and NP_077743 (variant C), and NM_024426 and NP_077744 (variant D)).

Other specific examples of the tumor-specific protein include PD-L1 and PD-L2, which are associated with immune checkpoint.

The tumor-specific proteins described herein are named following the GenBank database of the National Center for Biotechnology Information (NCBI) ([www.ncbi.nlm.nih.gov/genbank/]).

Examples of the antibody that may be contained in the conjugate of the present invention include, but not limited to, cetuximab, panitumumab, zalutumumab, nimotuzumab, trastuzumab, Ado-trastuzumab emtansine, tositumomab, rituximab, ibritumomab tiuxetan, daclizumab, gemtuzumab, alemtuzumab, a CEA-scan Fab fragment, an OC125 monoclonal antibody, ab75705, B72.3, bevacizumab, afatinib, axitinib, bosutinib, cabozantinib, ceritinib, crizotinib, dabrafenib, dasatinib, erlotinib, everolimus, ibrutinib, imatinib, lapatinib, lenvatinib, nilotinib, olaparib, palbociclib, pazopanib, pertuzumab, ramucirumab, regorafenib, ruxolitinib, sorafenib, sunitinib, temsirolimus, trametinib, vandetanib, vemurafenib, vismodegib, basiliximab, ipilimumab, nivolumab, pembrolizumab, MPDL3280A, pidilizumab (CT-011), MK-3475, BMS-936559, MPDL3280A (atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MEDI4736, MOXR0916, AMP-224, PDR001, avelumab (MSB0010718C), rHIgM12B7, ulocuplumab, BKT140, varlilumab (CDX-1127), ARGX-110, MGA271, lirilumab (BMS-986015, IPH2101), IPH2201, AGX-115, emactuzumab, CC-90002, and MNRP1685A, and fragments including antigen recognition sites thereof.

1.2. Core Particle

Surprisingly, the conjugate of the present invention can enhance the ability of the conjugate to kill tumor cells by conjugating the above-mentioned antibody molecule to the core particle. Further, when a magnetic particle or a fluorescent particle is selected as the core particle, in vivo imaging becomes possible, and not only the treatment of a tumor of a patient, but also diagnosis (e.g., recognition of the location of the conjugate, or recognition of the location of a tumor having bound thereto the conjugate) becomes possible. Through the in vivo imaging using the conjugate, the timing of irradiation with a near-infrared ray for PIT, a three-dimensional irradiation position in a living body, and an irradiation amount (irradiation time and dose) can be optimized, and the therapeutic effect of PIT can be enhanced.

The core particle to be used for the conjugate of the present invention is a particle having an average particle diameter of 100 nm or less. Herein, the "average particle diameter" of the particle is the average value of the particle diameters of 100 particles randomly measured in electron microscope images. When the average particle diameter of the core particle is more than 100 nm, it becomes difficult for the conjugate to be selectively distributed in tumor cells. The average particle diameter of the core particle is preferably 70 nm or less, more preferably 50 nm or less, still more preferably 25 nm or less. The lower limit of the average particle diameter of the core particle is not particularly limited, but is preferably 1 nm or more from the standpoint of producibility.

Preferred examples of the core particle to be used for the conjugate of the present invention include a magnetic particle and a semiconductor particle. An inorganic substance, such as a magnetic material or a semiconductor, generally has a higher absorption rate for a light beam having a wavelength of from 500 nm to 900 nm than an organic substance, and hence is preferred because of a larger amount of heat generation at the time of irradiation with a light beam having a wavelength of from 500 nm to 900 nm. The magnetic particle is preferably a particle containing iron oxide, a manganese compound, or a gadolinium compound because imaging by magnetic resonance imaging (MRI) becomes possible. In addition, in consideration of conjugation to the antibody molecule, the magnetic particle preferably has, on the surface thereof, a reactive functional group, such as an amino group or a carboxy group, or a protein-binding molecule, such as avidin, streptavidin, or protein A. As such magnetic particle, for example, a dispersion of superparamagnetic iron oxide particles is sold as the Nanomag-D-spio series from micromod.

A quantum dot is preferably used as the semiconductor particle because of high brightness and a small particle diameter. In addition, in consideration of conjugation to the antibody molecule, the semiconductor particle preferably has, on the surface thereof, a reactive functional group, such as an amino group or a carboxy group, or a protein-binding molecule, such as avidin, streptavidin, or protein A. A preferred example of such quantum dot is a semiconductor nanoparticle disclosed in Patent Literature 3, which has a core-shell structure including a core and a shell surrounding the core, wherein the core is made of $(AgIn)_xZn_{2(1-x)}S_2$ ("x" satisfies $0.4 \leq x \leq 0.95$, preferably $0.8 \leq x \leq 0.9$), wherein the shell is made of ZnS or ZnO, and wherein the semiconductor nanoparticle has a hydrophilic functional group formed of a carboxyl group, a sulfo group, or a salt thereof on the surface of the shell. Another preferred example of the quantum dot is a CdSe-based quantum dot having an amino group introduced to the surface of the particle (e.g., amino-PEG-QDs800; Thermo Fisher).

In the conjugate of the present invention, the number of the antibody molecules linked to the core particle is preferably 1 or more, and preferably 20 or less, more preferably 16 or less, still more preferably 12 or less, even more preferably 5 or less, per core particle. When the number of the antibody molecules linked to the core particle is excessively large, the size of the conjugate as a whole is increased, and hence it tends to be difficult for the conjugate to be selectively distributed in tumor cells. In addition, the lower limit of the number of the antibody molecules linked in 1 mg of the conjugate of the present invention is preferably $1.0 \times 10^{-12}$ mol/mg, more preferably $5.0 \times 10^{-12}$ mol/mg, still more preferably $1.0 \times 10^{-11}$ mol/mg. Meanwhile, the upper limit of the number of the antibody molecules linked in 1 mg of the conjugate of the present invention is preferably $1.0 \times 10^{-8}$ mol/mg, more preferably $5.0 \times 10^{-9}$ mol/mg, still more preferably $1.0 \times 10^{-9}$ mol/mg.

1.3. Photosensitive Portion

The conjugate of the present invention is preferably used as a drug for near-infrared photoimmunotherapy (NIR-PIT). Accordingly, the photosensitive portion to be used for the conjugate of the present invention is preferably a near-infrared ray (NIR)-sensitive portion. As described in Non Patent Literature 1, a related-art conjugate used for NIR-PIT is conceived to induce cell death in the following manner: the photosensitive portion of the conjugate bound to tumor cells becomes hydrophobic through NIR irradiation to cause aggregation of the conjugate, thereby disrupting the cell membranes of the tumor cells. In view of this mechanism, an example of the photosensitive portion to be used for the conjugate of the present invention is a portion showing increase of hydrophobicity when irradiated with NIR such as a light beam having a wavelength of from 500 nm to 900 nm.

For example, the photosensitive portion may contain: a photosensitive group having a maximum absorption wavelength at from 500 nm to 900 nm; and one or more hydrophilic functional groups linked or coordinated to the photosensitive group. When light having such wavelength is radiated, a photochemical reaction of the photosensitive group dissociates the hydrophilic functional group or causes a structural change, thus increasing the hydrophobicity of the photosensitive portion.

Examples of the hydrophilic functional group contained in the photosensitive portion include, but not limited to, a carboxylate ($—CO_2^-$) group, a sulfonate ($—SO_3^-$) group, a sulfonyl ($—SO_2^-$) group, a sulfate ($—SO_4^{-2}$) group, a hydroxy (—OH) group, a phosphate ($—OPO_3^{-2}$) group, a phosphonate ($—PO_3^{-2}$) group, an amino ($—NH_2$) group, and substituted or unsubstituted quaternary nitrogen (each having any counterion). Examples of the counterion include, but not limited to, sodium, potassium, calcium, ammonium, an organic amino salt, and a magnesium salt.

The photosensitive portion may further have a reactive group or linker for conjugation with the antibody molecule or the core particle.

Another example of the photosensitive portion to be used for the conjugate of the present invention is a portion containing a phthalocyanine skeleton. The photosensitive portion to be used for the conjugate of the present invention is preferably a portion containing a phthalocyanine skeleton. Phthalocyanine is an azaporphyrin containing four benzindole groups connected by nitrogen bridges in a 16-membered ring in which carbon atoms and nitrogen atoms are alternately arranged (i.e., $C_{32}H_{16}N_8$). Phthalocyanine forms a stable chelate with each of a metal cation and a non-metal cation, and in this case, the center of the ring is occupied by an ion (any one of a diamagnetic ion or a paramagnetic ion) capable of holding one or two ligands. The periphery of the ring may be unsubstituted or substituted.

It is preferred that the phthalocyanine to be used in the present invention be water-soluble and have at least one aqueous-solubilizing moiety. The aqueous-solubilizing moiety of the phthalocyanine preferably contains silicon. The phthalocyanine preferably has a core atom, such as Si, Ge, Sn, or Al, at the center of the ring.

The portion containing a phthalocyanine skeleton to be used in the present invention has a maximum absorption wavelength at preferably from 500 nm to 900 nm, more preferably from 600 nm to 850 nm, still more preferably from 660 nm to 740 nm. In addition, the portion containing a phthalocyanine skeleton preferably has one or more ligands each containing a hydrophilic functional group. Examples of the hydrophilic functional group include, but not limited to, a carboxylate ($—CO_2^-$) group, a sulfonate ($—SO_3^-$) group, a sulfonyl ($—SO_2^-$) group, a sulfate ($—SO_4^{-2}$) group, a hydroxy (—OH) group, a phosphate ($—OPO_3^{-2}$) group, a phosphonate ($—PO_3^{-2}$) group, an amino (—$NH_2$) group, and substituted or unsubstituted quaternary nitrogen (each having any counterion). Examples of the counterion include, but not limited to, sodium, potassium, calcium, ammonium, an organic amino salt, and a magnesium salt.

The portion containing a phthalocyanine skeleton to be used in the present invention preferably contains a linker having a reactive group capable of forming a bond between itself and the antibody molecule or the core particle. That is, the portion has a "linker-phthalocyanine skeleton moiety (L-D)" structure. The portion containing a phthalocyanine skeleton is preferably linked to the antibody molecule or the core particle via the linker substituted on the periphery of the ring of the phthalocyanine skeleton.

In a preferred embodiment, the portion containing a phthalocyanine skeleton to be used in the present invention is a compound represented by the following formula (Ia):

(Ia)

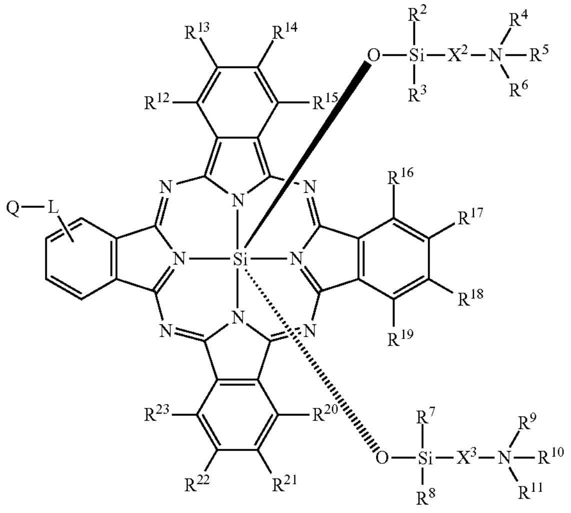

where:

L represents a direct bond or a linker;

Q represents a reactive group for forming a bond to the antibody molecule or the core particle;

$R^2$, $R^3$, $R^7$, and $R^8$ are each independently selected from a substituted or unsubstituted alkyl and a substituted or unsubstituted aryl;

$R^4$, $R^5$, $R^6$, $R^9$, $R^{10}$, and $R^{11}$, when present, are each independently selected from hydrogen, a substituted or unsubstituted alkyl, a substituted or unsubstituted alkanoyl, a substituted or unsubstituted alkoxycarbonyl, a substituted or unsubstituted alkylcarbamoyl, and a chelating ligand, wherein at least one of $R^4$, $R^5$, $R^6$, $R^9$, $R^{10}$, or $R^{11}$ contains a water-soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are each independently selected from hydrogen, a halogen, a substituted or unsubstituted alkylthio, a substituted or unsubstituted alkylamino, and a substituted or unsubstituted alkoxy, or at least one of i) $R^{13}$ and $R^{14}$, and carbon atoms to which $R^{13}$ and $R^{14}$ are bonded, ii) $R^{17}$ and $R^{18}$, and carbon atoms to which $R^{17}$ and $R^{18}$ are bonded, or iii) $R^{21}$ and $R^{22}$, and carbon atoms to which $R^{21}$ and $R^{22}$ are bonded, form a fused ring; and $X^2$ and $X^3$ each independently represent a $C_1$ to $C_{10}$ alkylene with or without an intervening heteroatom between carbon-carbon bonds. As used herein, the term "$C_1$ to $C_{10}$ alkylene" means a methylene group and alkylene groups having 2 to 10 carbon atoms.

In one embodiment, L represents a linker. In one embodiment, the linker is a linear or branched, cyclic or heterocyclic, saturated chain or unsaturated chain having 1 to 60 atoms, for example, 1 to 45 atoms or 1 to 25 atoms. In some cases, the atoms of the linker may each be selected from C, N, P, O, and S. In one embodiment, L may have additional hydrogen atoms satisfying a valence (in addition to the above-mentioned 1 to 60 atoms). In general, the linker may contain an ether, a thioether, an amine, an ester, a carbamate, urea, thiourea, carbonyl, an amide, a single bond, a double bond, a triple bond, an aromatic carbon-carbon bond, a phosphorus-oxygen bond, a phosphorus-sulfur bond, a nitrogen-nitrogen bond, a nitrogen-oxygen bond or a nitrogen-platinum bond, an aromatic bond, or a heteroaromatic bond, or any combination thereof.

In one embodiment, L is represented by the formula —$R^1$—Y—$X^1$—$Y^1$—, where: $R^1$ represents a divalent group or a direct bond; Y and $Y^1$ are each independently selected from a direct bond, oxygen, substituted or unsubstituted nitrogen, and sulfur; and $X^1$ is selected from a direct bond and a $C_1$ to $C_{10}$ alkylene with or without an intervening heteroatom between carbon-carbon bonds. Examples of the divalent group include, but not limited to, a substituted or unsubstituted alkylene, a substituted or unsubstituted alkyleneoxycarbonyl, a substituted or unsubstituted alkylenecarbamoyl, a substituted or unsubstituted alkylenesulfonyl, and a substituted or unsubstituted arylene.

Detailed examples of $R^1$ include, but not limited to, a substituted or unsubstituted alkylene, a substituted or unsubstituted alkyleneoxycarbonyl, a substituted or unsubstituted alkylenecarbamoyl, a substituted or unsubstituted alkylenesulfonyl, a substituted or unsubstituted alkylenesulfonylcarbamoyl, a substituted or unsubstituted arylene, a substituted or unsubstituted arylenesulfonyl, a substituted or unsubstituted aryleneoxycarbonyl, a substituted or unsubstituted arylenecarbamoyl, a substituted or unsubstituted arylenesulfonylcarbamoyl, a substituted or unsubstituted carboxyalkyl, a substituted or unsubstituted carbamoyl, carbonyl, a substituted or unsubstituted heteroarylene, a substituted or unsubstituted heteroaryleneoxycarbonyl, a substituted or unsubstituted heteroarylenecarbamoyl, a substituted or unsubstituted heteroarylenesulfonylcarbamoyl, a substituted or unsubstituted sulfonylcarbamoyl, thiocarbonyl, sulfonyl, and sulfinyl.

An alkylene contained in each of the substituted or unsubstituted alkylene, the substituted or unsubstituted alkyleneoxycarbonyl, the substituted or unsubstituted alkylenecarbamoyl, the substituted or unsubstituted alkylenesulfonyl, and the substituted or unsubstituted alkylenesulfonylcarbamoyl is preferably a $C_1$ to $C_{10}$ alkylene with or without an intervening heteroatom between carbon-carbon bonds.

In one embodiment, Q contains a reactive group for forming a bond to the antibody molecule or the core particle. As used herein, the term "reactive group" refers to a moiety on a compound capable of forming a bond by chemically reacting with a functional group on a different material (e.g., the antibody molecule). The reactive group is typically an electrophile or nucleophile capable of forming a covalent bond through exposure to a corresponding functional group serving as a nucleophile or an electrophile, respectively.

In one embodiment, Q contains a reactive group that is reactive with a carboxyl group, an amino group, or a thiol group on the target antibody molecule or core particle. Suitable examples of the reactive group include, but not limited to, an activated ester, a halogenated acyl, a halogenated alkyl, an anhydride, a carboxylic acid, a carbodiimide, a carbonate, a carbamate, a haloacetamide (e.g., iodoacetamide), an isocyanate, an isothiocyanate, maleimide, an N-hydroxysuccinimide (NHS) ester, a phosphoramidite, a platinum complex, a sulfonic acid ester, and a thiocyanate. In one embodiment, the reactive group is a sulfhydryl-reactive chemical group, for example, maleimide, haloacetyl, or pyridyl disulfide. In one embodiment, the reactive group is amine-reactive. In a preferred embodiment, the reactive group is an NHS ester.

In one embodiment, $R^2$, $R^3$, $R^7$, and $R^8$ each independently represent a substituted or unsubstituted alkyl, for example, a substituted or unsubstituted methyl, ethyl, or isopropyl.

In one embodiment, at least one of $R^4$, $R^5$, $R^6$, $R^9$, $R^{10}$, or $R^{11}$ contains a water-soluble group. In some cases, at least two of $R^4$, $R^5$, $R^6$, $R^9$, $R^{10}$, and $R^{11}$ each contain a water-soluble group, and in other cases, three or more thereof each contain a water-soluble group. In one embodiment, at least one of $R^4$, $R^5$, $R^6$, $R^9$, $R^{10}$, or $R^{11}$ represents an alkyl substituted with a water-soluble group. In one embodiment, $R^4$, $R^5$, $R^6$, $R^9$, $R^{10}$, and $R^{11}$ each independently represent a substituted or unsubstituted alkyl, and at least one, preferably two or more, thereof represents an alkyl substituted with a water-soluble group. In a preferred embodiment, $R^4$, $R^5$, $R^6$, $R^9$, $R^{10}$, and $R^{11}$ each independently represent a substituted or unsubstituted alkyl, at least one of $R^4$, $R^5$, or $R^6$ represents an alkyl substituted with a water-soluble group, and at least one of $R^9$, $R^{10}$, or $R^{11}$ represents an alkyl substituted with a water-soluble group.

As used herein, the term "water-soluble group" refers to a group containing one or a plurality of polar and/or ionic substituents, for improving the solubility of the molecule as a whole in an aqueous medium. Examples of the water-soluble group include, but not limited to, a carboxylate ($—CO_2^-$) group, a sulfonate ($—SO_3^-$) group, a sulfonyl ($—SO_2^-$) group, a sulfate ($—SO_4^{-2}$) group, a hydroxy (—OH) group, a phosphate ($—OPO_3^{-2}$) group, a phosphonate $—PO_3^{-2}$) group, an amino ($—NH_2$) group, and substituted or unsubstituted quaternary nitrogen (each having any counterion). Suitable examples of the counterion include, but not limited to, sodium, potassium, calcium, ammonium, an organic amino salt, and a magnesium salt. The counterion is preferably a biologically acceptable counterion.

The nitrogen atoms to which $R^4$, $R^5$, $R^6$, $R^9$, $R^{10}$, and $R^{11}$ are bonded may each be trivalent or tetravalent.

In one embodiment, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ each represent hydrogen.

In one embodiment, $X^2$ and $X^3$ each independently represent a $C_1$ to $C_{10}$ alkylene with or without an intervening heteroatom between carbon-carbon bonds. In one embodiment, nitrogen added to $X^2$ and/or $X^3$ may be quaternized.

In one preferred embodiment, the portion containing a phthalocyanine skeleton to be used in the present invention is a compound represented by the formula (Ib):

(Ib)

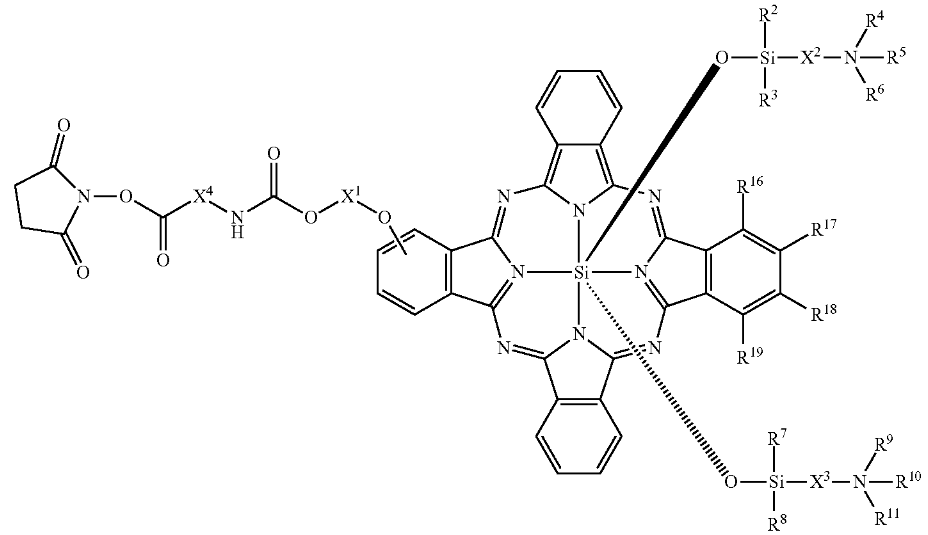

where:

$X^1$ and $X^4$ each independently represent a $C_1$ to $C_{10}$ alkylene with or without an intervening heteroatom between carbon-carbon bonds; and $R^2$, $R^3$, $R^4$, $R^5$, $R^6$, $R^7$, $R^8$, $R^9$, $R^{10}$, $R^{11}$, $R^{16}$, $R^{17}$, $R^{18}$, $R^{19}$, $X^2$, and $X^3$ are as defined for the above-mentioned formula (Ia).

In the compound of the above-mentioned formula (Ib), the reactive group for forming a bond to the antibody molecule or the core particle is an NHS ester. In one embodiment, the reactivity of the NHS ester may be controlled by changing the length of the alkylene group of $X^4$ present between the NHS ester and the carbamate functional group. In one embodiment, the length of the alkylene group of $X^4$ between the NHS ester and the carbamate functional group is inversely proportional to the reactivity of the NHS ester. In one embodiment, $X^4$ represents a $C_5$-alkylene. In another embodiment, $X^4$ represents a $C_3$-alkylene. In one embodiment, $X^1$ represents a $C_6$-alkylene. In another embodiment, $X^1$ represents a $C_3$-alkylene.

In one embodiment, the compound of the formula (Ia) or the formula (Ib) has a net charge of zero. In certain cases, the neutral charge may be obtained with one or a plurality of any counterions, or quaternized nitrogen.

In one embodiment, after the compound of the formula (Ia) or the formula (Ib) has been linked to the target antibody molecule or core particle, the target molecule or particle retains its solubility, and hence the conjugate has a sufficient solubility in an aqueous solution.

In one preferred embodiment, the portion containing a phthalocyanine skeleton to be used in the present invention is an IR700 NHS ester such as an IRDye 700DX NHS ester (LiCor 929-70010 or 929-70011). In one preferred embodiment, the portion containing a phthalocyanine skeleton is a compound represented by the following formula (II).

(II)

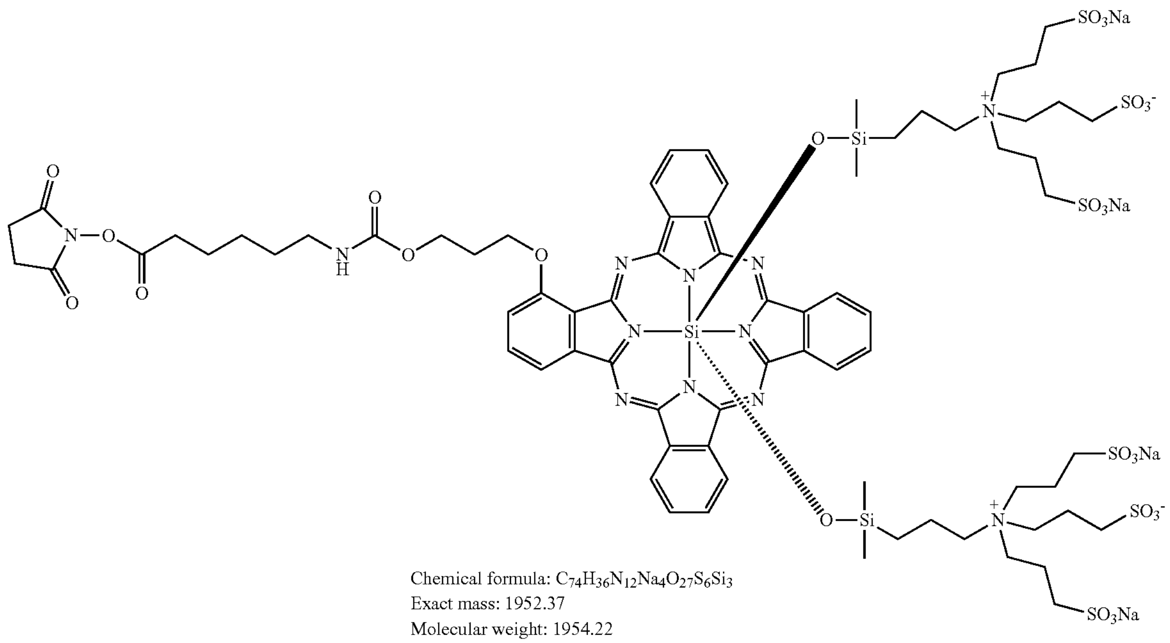

Chemical formula: $C_{74}H_{36}N_{12}Na_4O_{27}S_6Si_3$
Exact mass: 1952.37
Molecular weight: 1954.22
IRDye 700DX NHS ester In consideration of the purpose of the present invention, the above-mentioned photosensitive portion is contained in the conjugate of the present invention in a configuration of being linked via its reactive group to the target antibody molecule or core particle. For example, the compound represented by the above-mentioned formula (Ia), (Ib), or (II), "IR700", "IRDye 700DX", or any of modified forms thereof, which may be contained in the conjugate of the present invention, refers to those compounds in a configuration of being linked via the reactive group to the target antibody molecule or core particle. In general, IR700 has some preferred chemical characteristics. Amino-reactive IR700 is relatively hydrophilic, and can be covalently bonded to an antibody through use of the NHS ester of IR700. IR700 typically has an absorption coefficient ($2.1\times10^5\ M^{-1}\ cm^{-1}$ in terms of absorption maximum at 689 nm) 5 or more times as high as those of conventional photosensitizers, such as a hematoporphyrin derivative Photofrin (trademark) ($1.2\times10^3\ M^{-1}\ cm^{-1}$ at 630 nm), meta-tetrahydroxyphenylchlorin; Foscan (trademark) ($2.2\times10^4\ M^{-1}\ cm^{-1}$ at 652 nm), and mono-L-aspartyl chlorin e6; NPe6/Laserphyrin (trademark) ($4.0\times10^4\ M^{-1}\ cm^{-1}$ at 654 nm).

The portion containing a phthalocyanine skeleton to be used in the present invention, such as the compound represented by the above-mentioned formula (Ia), (Ib), or (II), may be produced using a commercially available starting material. For example, the skeleton is synthesized by fusing two or more different diiminoisoindolines. A synthesis strategy using different dinitriles or diiminoisoindolines can derive phthalocyanines having various degrees of substitution and/or regioisomers having various degrees of distribution. An exemplary synthetic scheme for generating a phthalocyanine skeleton is described in U.S. Pat. No. 7,005,518 B2.

In the conjugate of the present invention, the above-mentioned photosensitive portion only needs to be linked to at least one of the antibody molecule or the core particle, but is preferably linked to the antibody molecule. In addition, the conjugate of the present invention may comprise one or two or more of the above-mentioned photosensitive portions, and those photosensitive portions may have identical or different structures.

2. Method of Producing Conjugate

In the production of the conjugate of the present invention, it is preferred that, first, an antibody molecule and/or a core particle having a photosensitive portion be synthesized. Conjugation between the photosensitive portion and the antibody molecule or the core particle may be carried out by known means.

For example, as a specific technique for conjugating the portion containing a phthalocyanine skeleton and the antibody molecule, there is given a method disclosed in Patent Literature 1 or Example 1 to be described later. More specifically, it is appropriate that an aqueous phosphate solution containing the antibody molecule and the phthalocyanine compound represented by the above-mentioned formula (Ia) having an NHS ester in the reactive group Q (e.g., the above-mentioned IR700 NHS ester) be incubated at room temperature, and an antibody-photosensitive portion conjugate of interest be purified from the reaction liquid by column purification or the like.

When the portion containing a phthalocyanine skeleton and the core particle are linked to each other, for example, the compound represented by the above-mentioned formula (Ia) having an NHS ester in the reactive group Q, and the core particle having an amino group or a protein molecule, such as avidin, streptavidin, or protein A, introduced to the surface of the particle may be subjected to a reaction by a method similar to the foregoing.

The number of the photosensitive portions linked to the antibody molecule is preferably 1 or more, more preferably 2 or more, and preferably 5 or less, more preferably 4 or less, per antibody molecule. The number of the photosensitive portions linked to the core particle is preferably 1 or more, and preferably 80 or less, more preferably 50 or less, still more preferably 20 or less, per core particle.

Next, the antibody molecule and the core particle are linked to each other. Thus, the conjugate of the present invention may be produced. For example, the conjugate of the present invention may be produced by mixing the antibody molecule that has been biotinylated by a conventional method with the core particle having a substance that binds to biotin introduced to the surface of the particle, to thereby conjugate the antibody molecule to the core particle. Examples of the substance that binds to biotin include proteins, such as avidin and streptavidin. The substance that binds to biotin is introduced at preferably from 1 to 5, more preferably from 1 to 4, even more preferably from 1 to 3 molecules per core particle. Alternatively, as shown in Examples to be described later, the antibody molecule and the core particle may be subjected to a crosslinking reaction by utilizing a carbodiimide compound such as 1-ethyl-3-(3-dimethylaminopropyl)carbodiimide (EDC) and an N-hydroxysuccinimide derivative such as Sulfo-NHS. In this case, the loading amounts of the antibody molecule and the core particle are set so that the number of the antibody molecules linked per core particle may become a desired number (preferably 1 or more, and preferably 20 or less, more preferably 16 or less, still more preferably 12 or less, even more preferably 5 or less). In addition, the loading amount may be set so that the number of the antibody molecules linked per mg of the core particle may become a desired number. Specifically, the lower limit of the loading amount of the antibody molecule per mg of the core particle is preferably $1.0\times10^{-12}$ mol/mg, more preferably $5.0\times10^{-12}$ mol/mg, still more preferably $1.0\times10^{-11}$ mol/mg. Meanwhile, the upper limit of the loading amount of the antibody molecule per mg of the core particle is preferably $1.0\times10^{-8}$ mol/mg, more preferably $5.0\times10^{-9}$ mol/mg, still more preferably $1.0\times10^{-9}$ mol/mg. However, the conjugation between the antibody molecule and the core particle is not limited to a covalent bond, and may comprise conjugation based on, for example, a hydrogen bond, an ionic bond, a hydrophobic interaction, or a combination thereof.

2. Composition Comprising Conjugate

In one aspect, the present invention provides a composition comprising the above-mentioned conjugate of the present invention. In a preferred embodiment, the composition comprising the conjugate of the present invention (hereinafter sometimes referred to as "composition of the present invention") is used as a pharmaceutical composition for photoimmunotherapy (PIT).

In one embodiment, the composition of the present invention comprises the conjugate of the present invention and a pharmaceutically acceptable carrier or excipient. Examples of the pharmaceutically acceptable carrier include, but not limited to, water, an oil, a buffer, phosphate-buffered saline, and other diluents for injections. Examples of the excipient include, but not limited to, starch, glucose, lactose, dextrose, carboxymethyl cellulose, glycerol, propylene glycol, water, and ethanol. As required, the composition of the present invention may comprise a lubricant, a binder, a humectant, an emulsifier, a pH adjusting agent, an isotonic agent, a buffer, an antioxidant, a suspending agent, a solubility improver, a preservative, a chelating agent, and other pharmaceutically acceptable substances. The pharmaceutically acceptable carrier, excipient, and the like are known in the art (see, for example, Remington's Pharmaceutical Sciences, by E. W. Martin, Mack Publishing Co., Easton, Pa., 19th Edition, 1995).

It is appropriate that the composition of the present invention have a liquid form, for example, be a solution, a suspension, or a syrup; or have a solid form, for example, be a powder, a pill, a tablet, a capsule, a transdermal patch, an inhalant, or a suppository. Alternatively, the composition of the present invention may have a freeze-dried form and be administered by being reconstituted with a pharmaceutically acceptable carrier (e.g., a diluent for an injection) at the time of use. The composition having such liquid or solid form may be prepared in accordance with a conventional method. In one embodiment, the composition of the present invention is a one-part formulation comprising a carrier or excipient containing the conjugate of the present invention. In another embodiment, the composition of the present invention is a two-part formulation separately comprising: the conjugate of the present invention; and a diluent or the like to be administered therewith.

In a preferred embodiment, the composition of the present invention is a pharmaceutical composition. The form of the pharmaceutical composition may depend on its dosing regimen. The dosing regimen of the pharmaceutical composition may be appropriately designed in accordance with, for example, the kind and state of a tumor to be targeted, and the species, age, and state of a patient. The pharmaceutical composition may be an oral formulation or a parenteral formulation, and may be, for example, an injectable preparation, an oral preparation, or an external preparation. The pharmaceutical composition may be configured to be for single-time administration or for a plurality of times of administration. The content of the conjugate of the present invention in the pharmaceutical composition may be appropriately designed in accordance with, for example, the form of the pharmaceutical composition, and its dose for the patient.

The pharmaceutical composition is adjusted to a pH range compatible with an animal's body, for example, a pH of 5 or more, preferably a pH of 5.5 or more, and a pH of 10 or less, preferably a pH of 8 or less, more preferably a pH of 7.3 or less, or preferably a pH of from 5.5 to 10, more preferably a pH of from 5.5 to 8, still more preferably a pH of from 5.5 to 7.3. The pH of the composition may be adjusted with the above-mentioned pH adjusting agent, buffer, or the like.

In one embodiment, it is appropriate that the dose of the conjugate of the present invention in the pharmaceutical composition fall within the range of from 0.01 mg to 9,000 mg, for example, in the case of a formulation for injection. In one embodiment, it is appropriate that the dose of the pharmaceutical composition administered at a single time be from 0.5 mL to 1,000 mL, for example, in the case of a formulation for injection. In one embodiment, the pharmaceutical composition is a formulation for injection, its volume administered at a single time is from 1 mL to 5 mL, and the volume administered at a single time contains 0.1 mg to 5,000 mg of the conjugate of the present invention.

3. Treatment of Tumor Using Conjugate of the Present Invention

In another aspect, the present invention relates to a use of the conjugate of the present invention or the composition of the present invention comprising the conjugate, for treatment of a tumor by photoimmunotherapy (PIT). In one embodiment, the present invention provides the conjugate or the composition of the present invention, for use in treatment of a tumor by PIT. In another embodiment, the present invention provides a use of the conjugate or the composition of the present invention in production of a tumor therapeutic agent for PIT. In another embodiment, the present invention provides a method of treating a tumor by PIT through use of the conjugate or the composition of the present invention. The method of treating a tumor according to the present invention (hereinafter sometimes referred to as "treatment method of the present invention") comprises the steps of: administering the conjugate or the composition of the present invention to a patient; and irradiating the patient with a near-infrared ray (NIR). Accordingly, the PIT to be used in the present invention is specifically near-infrared photoimmunotherapy (NIR-PIT). Herein, the term "method of treating a tumor" may be replaced with the term "method of killing a tumor."

The patient to which the conjugate or the composition of the present invention is administered is a patient in need of treatment of a tumor. Examples of the patient include, but not limited to, a human and a non-human animal each having a tumor. Examples of the non-human animal include non-human mammals, such as a mouse, a rat, a hamster, a rabbit, a pig, a goat, a dog, a cat, a sheep, a bovine, and a horse. In addition, the patient may or may not have the experience of another treatment for a tumor (e.g., surgery, chemotherapy, or radiation therapy).

The antibody molecule contained in the conjugate of the present invention is selected in accordance with the kind of the tumor to be targeted. The antibody molecule can specifically bind to an antigen present on the surface of a target tumor cell, preferably a tumor-specific protein expressed on the surface of the tumor cell. Appropriate selection of the antibody molecule enables the conjugate of the present invention to accumulate in the target tumor. Cell surface antigens of various tumors to be targeted, such as the tumor-specific protein, may be decided in accordance with known information. A person skilled in the art can select an antibody molecule specific for a target antigen on the tumor to be treated.

3.1. Administration of Conjugate

The dosing regimen (e.g., administration route, dose, and number of times) of the conjugate or the composition of the present invention may be appropriately decided in accordance with, for example, the kind and state of the tumor to be targeted, and the species, age, and state of the patient. Examples of the administration route include: local administration to a tumor-affected area via injection, a catheter, spraying, application, a patch, a suppository, or the like; and systemic administration via infusion, oral administration, intraperitoneal administration, intravenous injection, or the like. It is preferred that the conjugate or the composition of the present invention be locally administered. In one embodiment, the conjugate or the composition of the present invention is intravenously administered. In one embodiment, the conjugate or the composition of the present invention is directly administered to the affected area of the tumor to be targeted through use of a syringe or the like, or is injected via a catheter.

The conjugate or the composition of the present invention may be used alone for the treatment of a tumor, but may be used in combination with another drug or therapy such as chemotherapy.

The conjugate or the composition of the present invention only needs to be administered in an effective amount to the patient. The "effective amount" refers to an amount allowing the conjugate of the present invention to accumulate in the tumor to be targeted of the patient in an amount sufficient for exhibiting the therapeutic effect of PIT. The "effective amount" preferably refers to such an amount that, while the therapeutic effect of PIT is exhibited in the patient, side effects on the patient can be minimized or kept within acceptable ranges.

The dosage of the conjugate of the present invention to the patient may be appropriately decided depending on the kind and state (location, volume, and the like) of the tumor to be targeted, and the species, age, and state of the patient, and the administration route, the form of the composition comprising the conjugate, and the like. For example, the dosage of the conjugate of the present invention may be set in accordance with the tumor volume. The tumor volume (V) may be calculated by, for example, measuring the short diameter (W) and long diameter (L) of the tumor and substituting the measured values into the equation: $V=(W^2 \times L)/2$. Alternatively, the dosage may be adjusted in accordance with the degree of accumulation of the conjugate of the present invention in the target tumor, which is measured by imaging to be described later. The dosage of the conjugate of the present invention for a human may be decided based on its dosage for a mouse. For example, when the conjugate of the present invention is administered to a human, its effective amount may be decided to be an amount that is from 5 to 10 times its effective amount in a mouse.

In one example, when the composition comprising the conjugate of the present invention is injected into a tumor-affected area of an adult (60 kg), the single dosage (injection amount) of the composition is generally from 1 mL to 5 mL. In another example, when the conjugate of the present invention is injected into a tumor-affected area of an adult (60 kg), the single dosage (injection amount) of the conjugate is from 0.01 mg/kg (body weight) to 20 mg/kg (body weight).

The dosage of the conjugate of the present invention and the number of times of administration thereof may be increased or decreased in accordance with a therapeutic effect on the tumor. The therapeutic effect on the tumor may be evaluated by a general evaluation method for tumor treatment, such as the shrinkage rate of a tumor tissue. In one embodiment, the conjugate of the present invention is administered a single time in the above-mentioned dosage. In another embodiment, the conjugate of the present invention is administered a plurality of times. In the case of a plurality of times of administration, the above-mentioned dosage may be repeatedly administered, or the dosage may be increased or decreased in accordance with the therapeutic effect on the tumor. In one embodiment, second or more time administration may be carried out after the clearance of the dose of the last administration from the patient. In another embodiment, the conjugate of the present invention may be repeatedly administered once in 1 week, once in 2 weeks, once in 1 month, or at a lower frequency. In another embodiment, the conjugate of the present invention may be administered again when the target tumor remains after 1 week, 2 weeks, 3 weeks, 4 weeks, 2 months, 6 months, 1 year, or more from the last administration.

3.2. Photo Immunotherapy

Subsequent to the administration of the conjugate or the composition of the present invention to the patient, the patient is irradiated with NIR. It is preferred that the tumor cell or tumor-affected area having bound thereto the conjugate of the present invention be locally irradiated with NIR. The conjugate of the present invention exposed to NIR causes a photochemical reaction to kill the tumor cell having bound thereto the conjugate. The conjugate of the present invention administered to the patient specifically binds to the target tumor cell via the antibody molecule. Accordingly, selective killing of the target tumor cell is achieved by the present invention.

The wavelength of the light beam to be radiated is preferably from 500 nm to 900 nm, more preferably from 600 nm to 850 nm, still more preferably from 660 nm to 740 nm.

The timing of the irradiation may be decided to be any timing after the administration of the conjugate of the present invention. For example, the timing may be decided to be any timing between 30 minutes and 96 hours after the administration, preferably between 30 minutes and 48 hours, between 30 minutes and 24 hours, between 1 hour and 48 hours, or between 1 hour and 24 hours after the administration.

The period of time of the irradiation may be appropriately decided within the range of from 5 seconds to 72 hours. The irradiation may be performed once or a plurality of times so that the cumulative irradiation time per administration of the conjugate of the present invention falls within the above-mentioned range. The period of time per irradiation may be appropriately decided, and may be set to, for example, 5 seconds, 10 seconds, 15 seconds, 20 seconds, 25 seconds, 30 seconds, 35 seconds, 40 seconds, 45 seconds, 50 seconds, or 55 seconds, or 1 minute, 1.5 minutes, 2 minutes, 2.5 minutes, 3 minutes, 3.5 minutes, 4 minutes, 4.5 minutes, or 5 minutes, or 10 minutes, 20 minutes, 30 minutes, 40 minutes, 50 minutes, or 60 minutes, or 1 hour or 2 hours.

In one embodiment, the dose of the NIR with which the patient is irradiated is preferably 1 $J/cm^2$ or more, more preferably 5 $J/cm^2$ or more, still more preferably 10 $J/cm^2$ or more, and preferably 1,000 $J/cm^2$ or less, more preferably 500 $J/cm^2$ or less, still more preferably 100 $J/cm^2$ or less, still more preferably 50 $J/cm^2$ or less, and for example, falls within the range of from 1 $J/cm^2$ to 1,000 $J/cm^2$, from 1 $J/cm^2$ to 500 $J/cm^2$, from 5 $J/cm^2$ to 200 $J/cm^2$, from 10 $J/cm^2$ to 100 $J/cm^2$, or from 10 $J/cm^2$ to 50 $J/cm^2$.

The irradiation may be carried out once or a plurality of times with respect to the administration of the conjugate of the present invention performed once. Accordingly, the irradiation may be completed at one time, or may be repeatedly performed over several days. When the irradiation is performed a plurality of times, the conditions for the respective times of irradiation may be identical to or different from each other. The dose, conditions, or method for the irradiation may be changed in accordance with the kind and state of the tumor.

3.3. Imaging

When the core particle of the conjugate of the present invention is a magnetic particle or a fluorescent particle (e.g., a semiconductor particle), in vivo imaging becomes possible. In one embodiment, the conjugate or the composition of the present invention is used for imaging of a patient or a tumor. For example, the conjugate or the composition of the present invention administered to a patient is used for imaging of a tumor before treatment of the tumor. The imaging of the tumor enables the recognition of the location of the conjugate in the body of the patient, or the location of the tumor having bound thereto the conjugate, that is, enables the diagnosis of the patient. Consequently, the timing of photoirradiation for PIT, a three-dimensional irradiation position in a living body, and an irradiation dose (irradiation time and dose) can be optimized, and the therapeutic effect of PIT can be enhanced.

As means for the imaging, there are given, for example, MRI and fluorescence imaging. The use of a magnetic particle containing, for example, iron oxide or a gadolinium compound serving as an MRI contrast agent as the core particle enables imaging by MRI. The imaging by MRI may be performed by a conventional method. Alternatively, the use of a fluorescent particle as the core particle enables fluorescence imaging. In the fluorescence imaging, excitation light for exciting the fluorescent particle is radiated. The wavelength of the excitation light to be radiated may be appropriately selected in accordance with the fluorescent particle to be used. Fluorescence emitted from the fluorescent particle is detected with a detector. The detector is not particularly limited, but examples thereof include a CCD camera, an optical CT apparatus, an endoscope, and a fundus camera. Examples of the fluorescent particle include: the semiconductor nanoparticle disclosed in Patent Literature 3; and a CdSe-based quantum dot having an amino group introduced to the surface of the particle. From the standpoint of simpleness, in the present invention, it is preferred that imaging by MRI be performed using a conjugate comprising a magnetic particle as the core particle.

3.4. Other Methods

The techniques for PIT and imaging each using the conjugate or the composition of the present invention described above are applicable not only in vivo, but also in vitro. For example, not only a tumor present in a patient's body, but also cultured tumor cells or a cultured tissue containing tumor cells may be subjected to the administration of the conjugate or the composition of the present invention and NIR irradiation to reduce the tumor cells or inhibit the growth thereof. A method for the administration of the conjugate or the composition of the present invention and conditions for the NIR irradiation may be appropriately changed in accordance with the state of the cells or tissue to be targeted. For example, the conjugate or the composition of the present invention may be directly administered to tumor cells in a culture product. Milder conditions may be selected for the dosage of the conjugate or the composition or the conditions for the NIR irradiation as compared to the case of the administration or irradiation for a patient.

EXAMPLES

The present invention is described in more detail below by way of Examples. However, the present invention is by no means limited to these Examples and the like.

Example 1: Production of Conjugate

1) Synthesis of Panitumumab Having Linked thereto IRDye 700DX (IR700)

2 mg (13.6 nmol) of a human monoclonal antibody panitumumab was incubated together with 133.6 μg (68.4 nmol, 5 mmol/L DMSO) of IRDye 700DX NHS Ester (manufactured by LI-COR Biosciences) in 0.2 mol/L $Na_2HPO_4$ (pH 8.5) at room temperature for from 30 minutes to 120 minutes. The mixture was purified with a Sephadex G50 column (PD-10; GE Healthcare, Piscataway, NJ). A protein concentration was determined with a Coomassie Plus protein assay kit (Pierce Biotechnology, Rockford, IL) by measuring absorption at 595 nm with a UV-Vis system (8453 Value system; Agilent Technologies, Palo alto, Calif.). The concentration of IR700 was measured based on absorption according to a UV-Vis system (Shimadzu UV-VIS). The number of IR700 was about 3 molecules per molecule of panitumumab. Panitumumab having linked thereto IR700 is hereinafter referred to as Pan-IR700.

2) Biotinylation of Pan-IR700

5.69 mg of (+)-biotin N-hydroxysuccinimide ester (manufactured by Sigma-Aldrich, hereinafter sometimes referred to as "Biotin-NHS") was dissolved in 1 mL of DMSO (manufactured by Sigma-Aldrich). 1 mL of a Pan-IR700 solution (2.0 mg/mL) was taken in a microtube, 8 μL of the previously prepared Biotin-NHS DMSO solution ([Biotin-NHS]/[Pan-IR700]=10) was added, and the mixture was left to stand still at room temperature for 3 hours. Unreacted biotin was removed through an ultrafiltration filter (Amicon Ultra 100 k), and the residue was adjusted to 1.9 mg/mL with Dulbecco's Phosphate Buffered Saline (manufactured by FUJIFILM Wako Pure Chemical Corporation, hereinafter sometimes referred to as "D-PBS") to provide biotinylated Pan-IR700. The biotinylated Pan-IR700 is hereinafter referred to as Pan-IR700-Biotin.

3) Production of Conjugate of Pan-IR700 and Magnetic Particles 120 mg (5 mg/mL, 24 mL) of Nanomag-D-Spio 79-19-201 (manufactured by Micromod, streptavidin surface-modified magnetic particles, particle diameter: 20 nm) was taken in a 50 mL tube, 1.8 mg (1.9 mg/mL, 947 μL) of Pan-IR700-Biotin was added, and the mixture was stirred at room temperature for 60 minutes. Further, 18 μg (0.1 mg/mL, 180 μL) of biotin (manufactured by FUJIFILM Wako Pure Chemical Corporation) was added, and the mixture was stirred at room temperature for 30 minutes. Thus, a dispersion containing a conjugate in which Pan-IR700 and the magnetic particles were linked was obtained. 1 mL of the above-mentioned dispersion was passed through an MS-columns (manufactured by Miltenyi Biotec) column placed on a magnetic stand to adsorb the conjugate having the magnetic particles linked therein onto the column. After that, 2 mL of D-PBS was passed through the column. This operation was carried out 4 times in total. The filtrate at the fourth time was irradiated with excitation light having a wavelength of 676 nm, and fluorescence at 700 nm was measured. As a result, it was recognized that no unreacted Pan-IR700-Biotin was detected. Thus, a conjugate of Pan-IR700 and the magnetic particles was produced. The resultant conjugate is hereinafter referred to as Nanomag-Pan-IR700.

In Nanomag-D-Spio 79-19-201, the particle concentration was $8.0\times10^{14}$ particles/mL ($1.6\times10^{14}$ particles/mg), and the conjugation amount of streptavidin was 1.5 μg/mg. On the basis of this, it was calculated that, in Nanomag-D-Spio 79-19-201, about 1.1 molecules of streptavidin (tetramer) were linked on average per magnetic particle. In addition, in the synthesis of Nanomag-Pan-IR700, the loading amount of Pan-IR700-Biotin was 3.5 times ($1.0\times10^{-10}$ mol, per mg of the magnetic particles) in terms of molar ratio with respect to the streptavidin (tetramer) in Nanomag-D-Spio 79-19-201.

4) Production of Conjugate of Pan-IR700 and Quantum Dots 1.0 mg (2.0 mg/mL, 500 μL) of Pan-IR700 and 0.4 mg of 1-ethyl-3-(3-dimethylaminopropyl)carbodiimide (EDC) (manufactured by Thermo Fisher, final concentration: 2 mM) were taken in a microtube, and were subjected to a reaction in 0.1 M MES buffer (under the condition of pH=4.7). Then, 1.1 mg of Sulfo-NHS (manufactured by Thermo Fisher, final concentration: 5 mM) was added, and the mixture was subjected to a reaction at room temperature for 15 minutes. Next, excess EDC and Sulfo-NHS were removed using ultrafiltration (Amicon Ultra 100 kDa, manufactured by Merck, 14,000×g, 10 min) to provide Pan-IR700 having bonded thereto a Sulfo-NHS ester. To the resultant compound, 170 μL of CdSe-based quantum dots amino-PEG-QDs800 (manufactured by Thermo Fisher, particle diameter: 20 nm, 8 μM) were added, and the mixture was left to stand still at room temperature overnight. Finally, excess Pan-IR700 was removed using ultrafiltration (Nanosep 300 kDa, manufactured by Pall, 1,000×g, 30 min). Thus, a conjugate of Pan-IR700 and the quantum dots was produced. The resultant conjugate is hereinafter referred to as QDs800-Pan-IR700.

In amino-PEG-QDs800, the particle concentration is 8 μM. On the basis of this, the loading amount of Pan-IR700 allowed to react with the quantum dots was about 4.9 molecules per quantum dot particle.

Comparative Example 1: Production of Conjugate of Pan-IR700 and Magnetic Particles (Particle Diameter>100 nm)

10 mg (10 mg/mL, 1 mL) of paramagnetic iron oxide particles Magnosphere SS015 streptavidin (manufactured by JSR Life Sciences, particle diameter: 150 nm) were taken in each of three tubes, and 68 μg, 135 μg, and 405 μg (1.9 mg/mL) of Pan-IR700-Biotin were added thereto, respectively. The mixtures were stirred at room temperature for 60 minutes to produce three kinds of conjugatees having different Pan-IR700 coating ratios. The three kinds of conjugatees are hereinafter referred to as Magnosphere-Pan-IR700-A, Magnosphere-Pan-IR700-B, and Magnosphere-Pan-IR700-C, respectively.

In the synthesis of Magnosphere-Pan-IR700-A to C, the loading amounts of Pan-IR700-Biotin were $4.5\times10^{-11}$ mol, $9.0\times10^{-11}$ mol, and $2.7\times10^{-10}$ mol, respectively, per mg of the magnetic particles.

Example 2: Evaluation of Biodistribution of Conjugate $6\times10^{6}$ cells/100 μL of cells (hereinafter sometimes referred to as "A431-Luc-GFP"), which were obtained by transfecting epidermal growth factor (EGFR)-expressing A431 (human epidermoid carcinoma-derived cells) with a luciferase and green fluorescent protein were subcutaneously injected near the right groin of a female homozygous athymic nude mouse, and were engrafted for 5 days.

After the 5 days, the mouse was anesthetized, and Nanomag-Pan-IR700 produced in Example 1 was administered into the tail vein at 111.1 μL/body (30 μg/body in terms of the antibody, 13.3 mg/body in terms of the particles). Fluorescence observation of the whole body of the mouse was performed at a wavelength of 700 nm with Pearl Trilogy (manufactured by LI-COR) from before the administration to 48 hours after the administration to examine the biodistribution of IR700. The fluorescence imaging of the whole body of the mouse is shown in FIG. 1. An increase in fluorescence was observed in a tumor-affected area (arrows in the figure), indicating the accumulation of the conjugate in the affected area.

Figure 2:
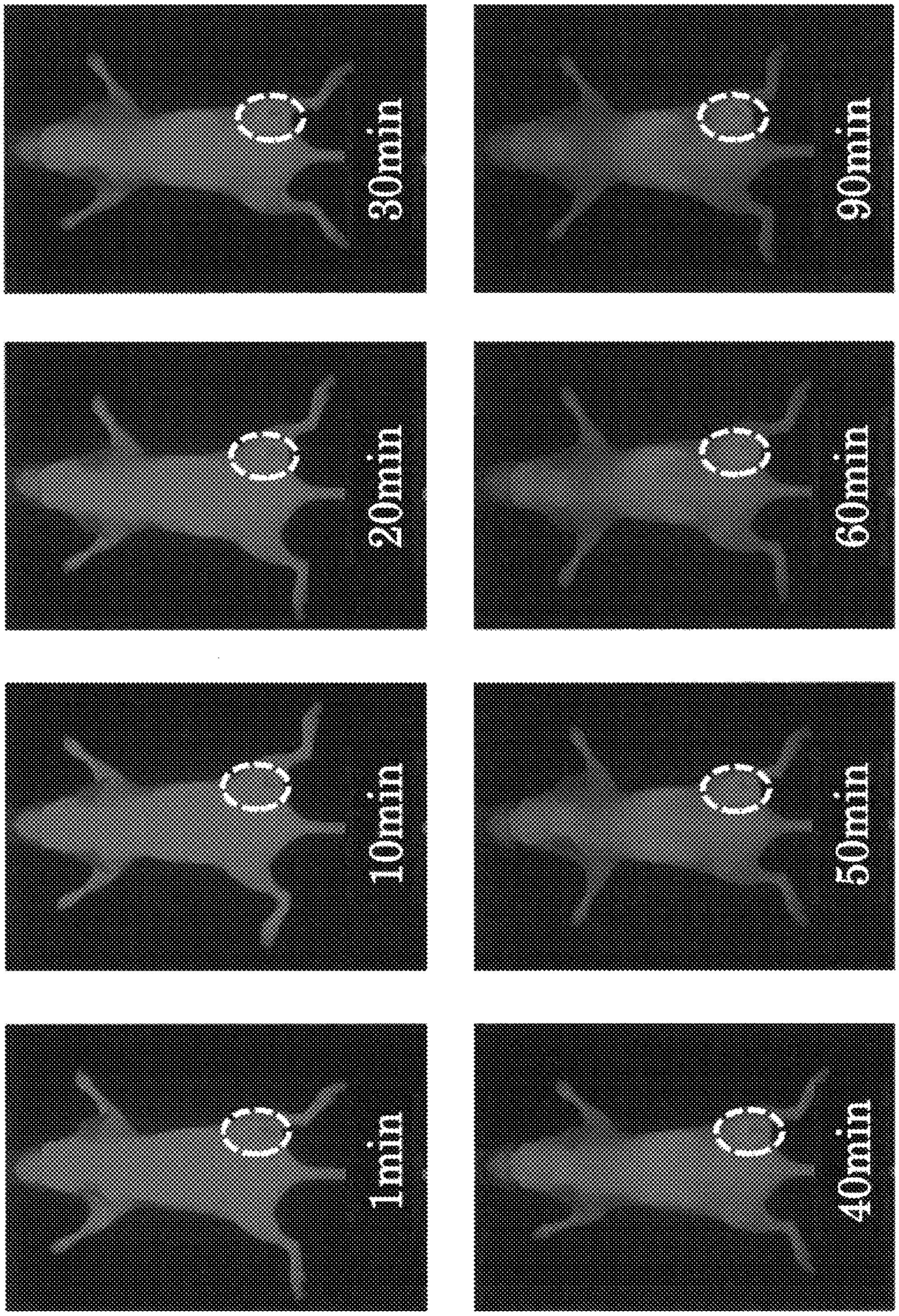
FIG. 2 shows fluorescence imaging of a tumor cell-implanted mouse administered QDs800-Pan-IR700. Fluorescence images of the whole body of the mouse from 1 minute (1 min) to 90 minutes (90 min) after the administration are shown. Dotted-line encirclements each indicate the injection site of tumor cells.

Similarly, QDs800-Pan-IR700 produced in Example 1 was administered into the tail vein of a mouse at 30 μg/body in terms of the antibody, and fluorescence observation was performed at 800 nm to examine the biodistribution of IR700. The fluorescence imaging of the whole body of the mouse is shown in FIG. 2. An increase in fluorescence was observed in a tumor-affected area (dotted-line encirclements in the figure), indicating the accumulation of the conjugate in the affected area.

Figure 3:
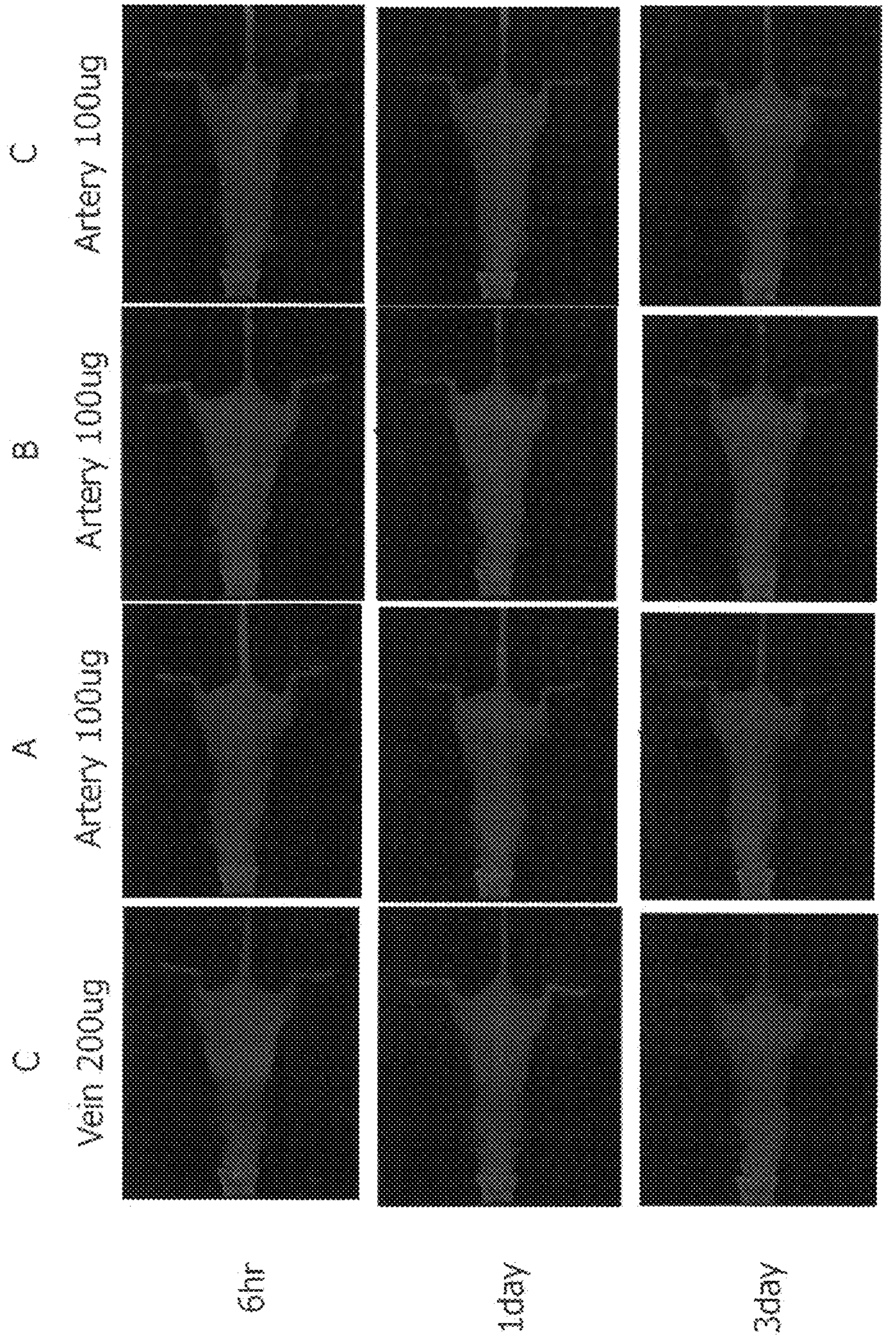
FIG. 3 shows fluorescence imaging of tumor cell-implanted mice administered conjugates of Comparative Example 1. Fluorescence images of the whole bodies of the mice after 6 hours, 1 day, and 3 days from the administration are shown.

Similarly, Magnosphere-Pan-IR700-A, Magnosphere-Pan-IR700-B, and Magnosphere-Pan-IR700-C produced in Comparative Example 1 were each intraarterially administered to a mouse at 100 μg/body in terms of the antibody, and the biodistribution of IR700 was examined by fluorescence observation. In addition, Magnosphere-Pan-IR700-C was administered into the tail vein of a mouse at 200 μg/body in terms of the antibody, and the biodistribution of IR700 was examined by fluorescence observation. As shown in FIG. 3, accumulations of the conjugatees in tumor-affected areas were not observed.

Example 3: In Vitro PIT with Conjugate

A431-Luc-GFP was cultured in RPMI1640 medium supplemented with 10% fetal bovine serum and 1% penicillin/streptomycin in a tissue culture flask in a humidified incubator at 37° C. under an atmosphere of 95% air and 5% carbon dioxide. $2\times10^{5}$ cultured cells were seeded in the four corners and central part of a 12-well plate together with 300 μL of RPMI-1640 medium supplemented with 10% fetal bovine serum and 1% penicillin/streptomycin, and were incubated for 6 hours.

To the prepared culture products, Nanomag-Pan-IR700, QDots-Pan-IR700, and Pan-IR700 produced in Example 1 were added at 10 μg/mL in terms of the antibody, followed by incubation at 37° C. over 24 hours. After that, the cells were washed with 500 μL of phosphate buffered saline (PBS), and then the culture medium was replaced with a phenol red-free medium.

Figure 4:
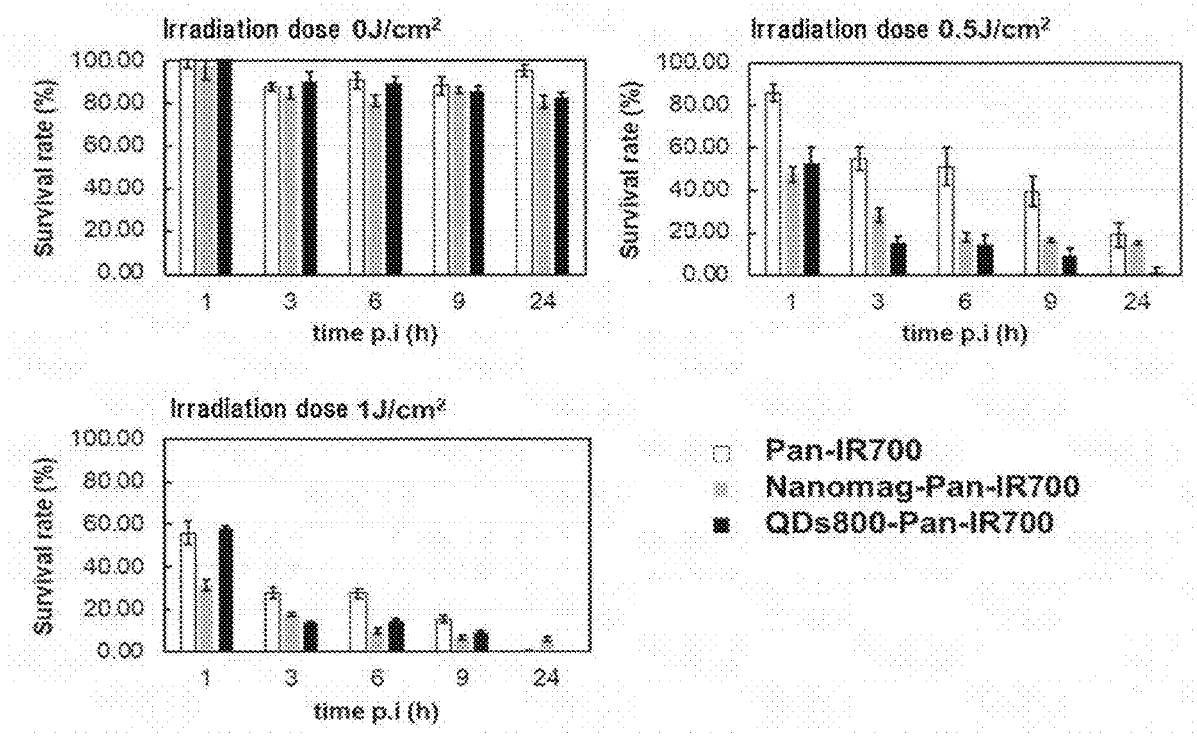
FIG. 4 shows the inhibition of survival of tumor cells by in vitro PIT. The horizontal axis of each graph represents time from conjugate administration, and the vertical axis thereof represents a cell survival rate.

Then, the four corners of the 12-well plate each containing the culture product were irradiated with near-infrared light having a wavelength of 690 nm at 0.5 $J/cm^2$ (18 $mW/cm^2\times30$ s) or 1 $J/cm^2$ (18 $mW/cm^2\times60$ s) through use of an LED, and then 200 μL of a luciferin was added. Periodically after the irradiation, light emission from the culture product was measured with a plate reader, and a viable cell count was calculated. The central part of the 12-well plate was used as an unirradiated control. The survival rate of the cells was determined from a light emission amount as compared to the control. The results are shown in FIG. 4. Each of the conjugatees reduced the cell survival rate, but the magnetic particle- or quantum dot-containing conjugatees Nanomag-Pan-IR700 and QDots-Pan-IR700 remarkably reduced the cell survival rate as compared to Pan-IR700 particularly after 3 hours or more from the irradiation.

Example 4: In Vivo PIT with Conjugate

Cells (hereinafter sometimes referred to as "MDA-MB-468-Luc-GFP"), which were obtained by transfecting epidermal growth factor (EGFR)-expressing MDA-MB-468 (human breast cancer-derived cells) with a luciferase and green fluorescent protein, were subcutaneously injected at $1\times10^7$ cells/100 μL near the right groin of three female homozygous athymic nude mice, and were engrafted for 3 weeks. After that, two of the mice were anesthetized, and Nanomag-Pan-IR700 produced in Example 1 was administered into the tail vein of each mouse at 80 μL/body (30 μg/body in terms of the antibody). After 1 day, the two mice were irradiated with a laser having a wavelength of 690 nm at 100 J/cm$^2$ (470 mW/cm$^2$) and 200 J/cm$^2$ (470 mW/cm$^2$), respectively, and tumor luciferase activities (emission intensities) before and after the irradiation were measured using an IVIS imaging system (PerkinElmer). Similarly, the other mouse was anesthetized, Pan-IR700 produced in Example 1 was administered into the tail vein at 60 μL/body (30 μg/body in terms of the antibody), and after 1 day, the mouse was irradiated with a laser having a wavelength of 690 nm at 200 J/cm$^2$ (470 mW/cm$^2$), and emission intensities before and after the irradiation were measured.

The emission intensities after the irradiation in the case where the emission intensities before the irradiation are defined as 100 are shown in Table 1. A higher emission intensity means a larger size of the tumor. As apparent from Table 1, a significant shrinkage of the tumor was recognized with the magnetic particle-containing conjugate Nanomag-Pan-IR700.

TABLE 1

| | Irradiation | Emission intensity (%) | |
|---|---|---|---|
| | dose (J/cm$^2$) | Before irradiation | After irradiation |
| Nanomag-Pan-IR700 | 100 | 100 | 4 |
| Nanomag-Pan-IR700 | 200 | 100 | 24 |
| Pan-IR700 | 200 | 100 | 886 |

Example 5: Evaluation of Heat Generation Behavior of Conjugate

Nanomag-Pan-IR700 produced in Example 1 was taken in a microtube in an amount of 1 μg in terms of the antibody, and PBS was added thereto to produce 50 μL of a Nanomag-Pan-IR700 solution. Pan-IR700 produced in Example 1 was taken in another microtube in an amount of 1 μg in terms of the antibody, and PBS was added thereto to produce 50 μL of a Pan-IR700 solution. As a control, 50 μL of PBS was taken in a microtube. The above-mentioned microtubes were left to stand still on ice for a while, and then each microtube was irradiated on ice with a laser having a wavelength of 690 nm at 282 J/cm$^2$ (470 mW/cm$^2\times$600 sec). Liquid temperatures before and after the irradiation were measured using a compact thermography camera FLIR C2.

The results of the measurement are shown in Table 2. As apparent from Table 2, in the Nanomag-Pan-IR700 solution, a temperature increase of more than 30° C. was recognized as a result of the irradiation with near-infrared light. This heat generation was conceived to be one of the factors in enhancing the effect of PIT.

TABLE 2

| | Liquid temperature before irradiation | Liquid temperature after irradiation |
|---|---|---|
| Nanomag-Pan-IR700 | −6.9° C. | 27.2° C. |
| Pan-IR700 | −5.9° C. | −4.4° C. |
| PBS | −7.4° C. | −6.8° C. |

Example 6: Imaging with Conjugate

1) MRI

Figure 5:
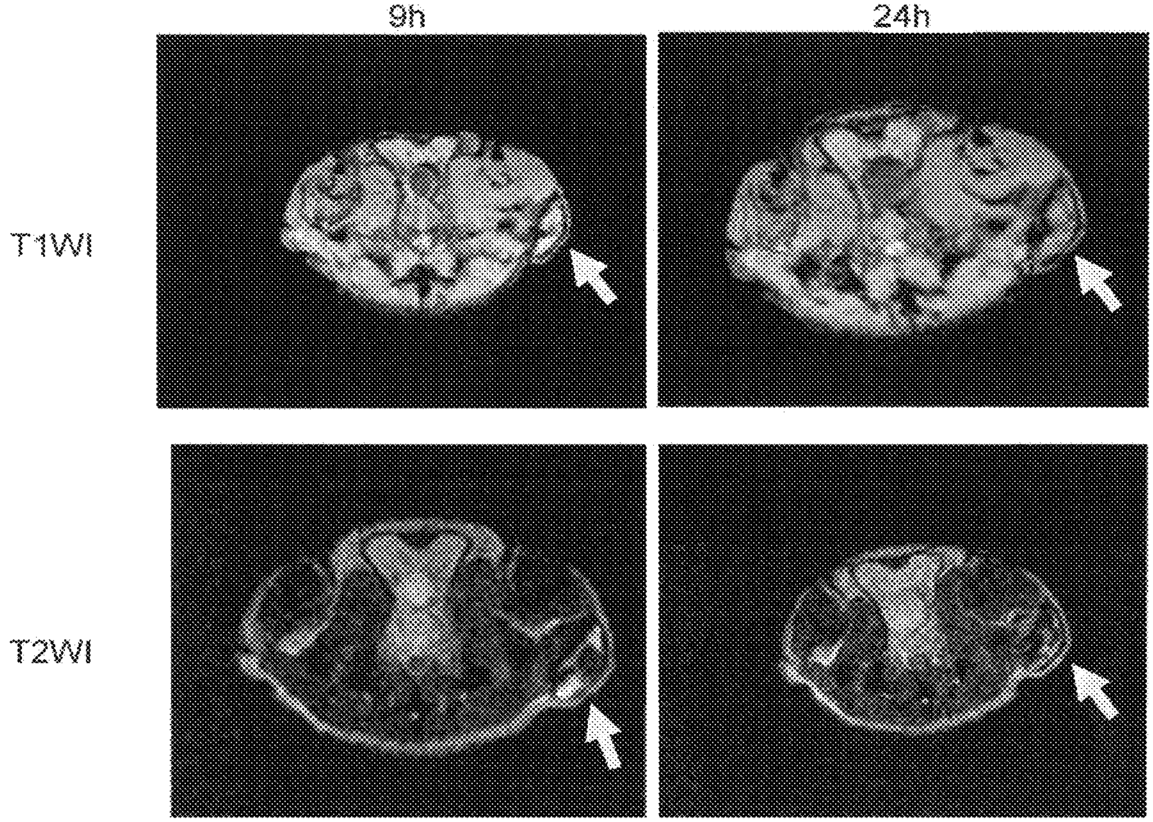
FIG. 5 shows MRI imaging of a tumor cell-implanted mouse administered Nanomag-Pan-IR700. MRI images at 9 hours and 24 hours after the administration are shown. Arrows each indicate the engraftment site of tumor cells.

Imaging performance in MRI was evaluated for the mouse administered Nanomag-Pan-IR700 in Example 2. 3T MRI-MRS 3000 (MR Solutions) was used as an MRI apparatus, and measurement was performed under T1WI (TR 250 msec, TE 6.0 msec, FA 90 deg) and T2WI (TR 2,000 msec, TE 69.0 msec, FA 90 deg). MRI images taken are shown in FIG. 5.

2) Confocal Microscopic Observation

As a model of normal non-target cells, 3T3-RFP cells were prepared by transfecting a cultured cell line of mouse skin-derived fibroblasts with (EF1a)-Puro lentiviral particles (AMSBIO, Cambridge, MA, USA) expressing red fluorescent protein (RFP) serving as a marker.

EGFR-expressing A431 (human epidermoid carcinoma-derived cells), MDAMB468 (human breast cancer-derived cells), and PC9 (human lung cancer-derived cells) were each mixed with the 3T3-RFP cells. Each cell mixture was seeded in a 12-well plate at $5\times10^4$ cells per well together with 300 μL of RPMI1640 medium supplemented with 10% fetal bovine serum and 1% penicillin/streptomycin, and was incubated for 24 hours. After that, to the culture product, Nanomag-Pan-IR700 was added at 10 μg/mL in terms of the antibody, the mixture was incubated for 1 hour and washed with 500 μL of PBS, and then the culture medium was replaced with a phenol red-free medium. Then, the culture product was irradiated with near-infrared light of 690 nm at 4 J/cm$^2$ (18 mW/cm$^2\times$240 s) using an LED, and fluorescence of the cells before and after the irradiation was observed with A1R-s Confocal Microscope (manufactured by Nikon).

Further, necrotic cells were observed using Sytox blue (manufactured by Thermo Fisher). As a result, cell death was recognized in all the cancer cells after the irradiation, whereas the normal cells (3T3-RFP cells) were recognized to be viable because the fluorescence (expression of RFP) of the cells was observed with no change even after the irradiation.

The invention claimed is:

1. A conjugate comprising:

A) an antibody molecule linked to a a compound represented by the following formula (Ia):

(Ia)

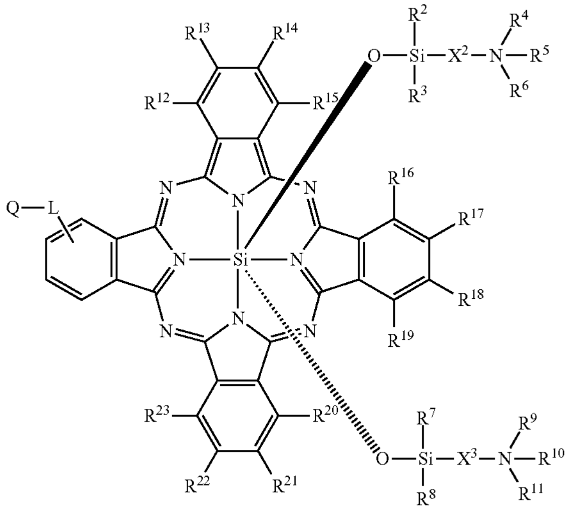

where:

L represents a direct bond or a linker;

Q represents a reactive group for forming a bond to the antibody molecule or the particle;

$R^2$, $R^3$, $R^7$, and $R^8$ are each independently selected from a substituted or unsubstituted alkyl and a substituted or unsubstituted aryl;

$R^4$, $R^5$, $R^6$, $R^9$, $R^{10}$ and $R^{11}$, when present, are each independently selected from hydrogen, a substituted or unsubstituted alkyl, a substituted or unsubstituted alkanoyl, a substituted or unsubstituted alkoxycarbonyl, a substituted or unsubstituted alkylcarbamoyl, and a chelating ligand, wherein at least one of $R^4$, $R^5$, $R^6$, $R^9$, $R^{10}$, or $R^{11}$ contains a water-soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are each independently selected from hydrogen, a halogen, a substituted or unsubstituted alkylthio, a substituted or unsubstituted alkylamino, and a substituted or unsubstituted alkoxy, or at least one of i) $R^{13}$ and $R^{14}$, and carbon atoms to which $R^{13}$ and $R^{14}$ are bonded, ii) $R^{17}$ and $R^{18}$, and carbon atoms to which $R^{17}$ and $R^{18}$ are bonded, or iii) $R^{21}$ and $R^{22}$, and carbon atoms to which $R^{21}$ and $R^{22}$ are bonded, form a fused ring; and $X^2$ and $X^3$ each independently represent a $C_1$ to $C_{10}$ alkylene with or without an intervening heteroatom between carbon-carbon bonds; and B) a magnetic particle or a semiconductor particle having an average particle diameter of 100 nm or less, which is linked to the antibody molecule:

wherein at least one of the antibody molecule or the particle is linked to a portion showing increase of hydrophobicity when irradiated with a light beam having a wavelength of from 500 nm to 900 nm.

2. The conjugate according to claim 1, wherein the antibody molecule is linked to the portion showing increase of hydrophobicity when irradiated with a light beam having a wavelength of from 500 nm to 900 nm.

3. The conjugate according to claim 1, wherein the compound represented by the formula (Ia) is a compound represented by the following formula (Ib):

(Ib)

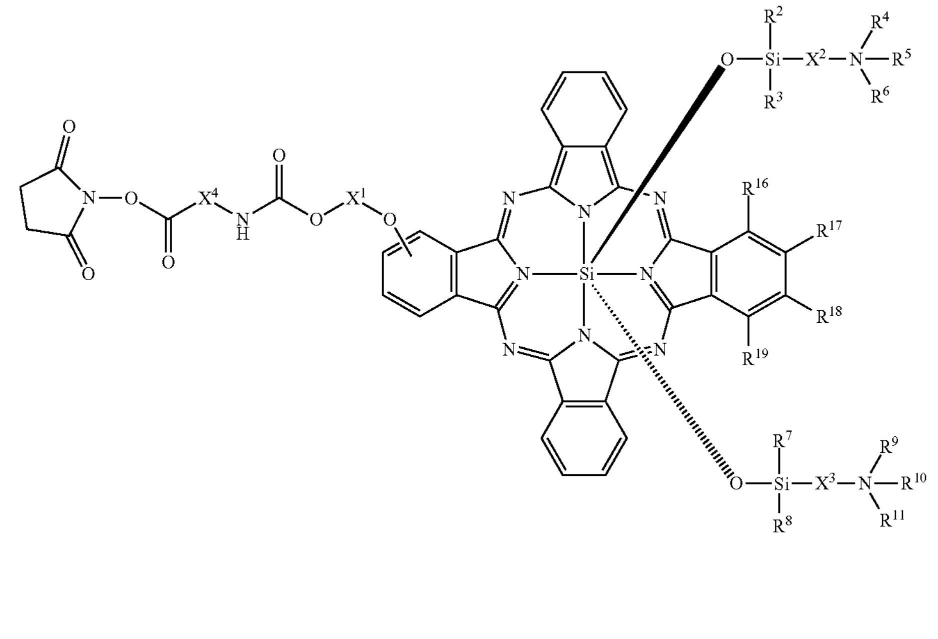

where:

$X^1$ and $X^4$ each independently represent a $C_1$ to $C_{10}$ alkylene with or without an intervening heteroatom; and $R^2$, $R^3$, $R^4$, $R^5$, $R^6$, $R^7$, $R^8$, $R^9$, $R^{10}$, $R^{11}$, $R^{16}$, $R^{17}$, $R^{18}$, $R^{19}$, $X^2$, and $X^3$ are as defined in claim 1.

4. The conjugate according to claim 1, wherein the compound represented by the formula (Ia) is a compound represented by the following formula (II).

(II)

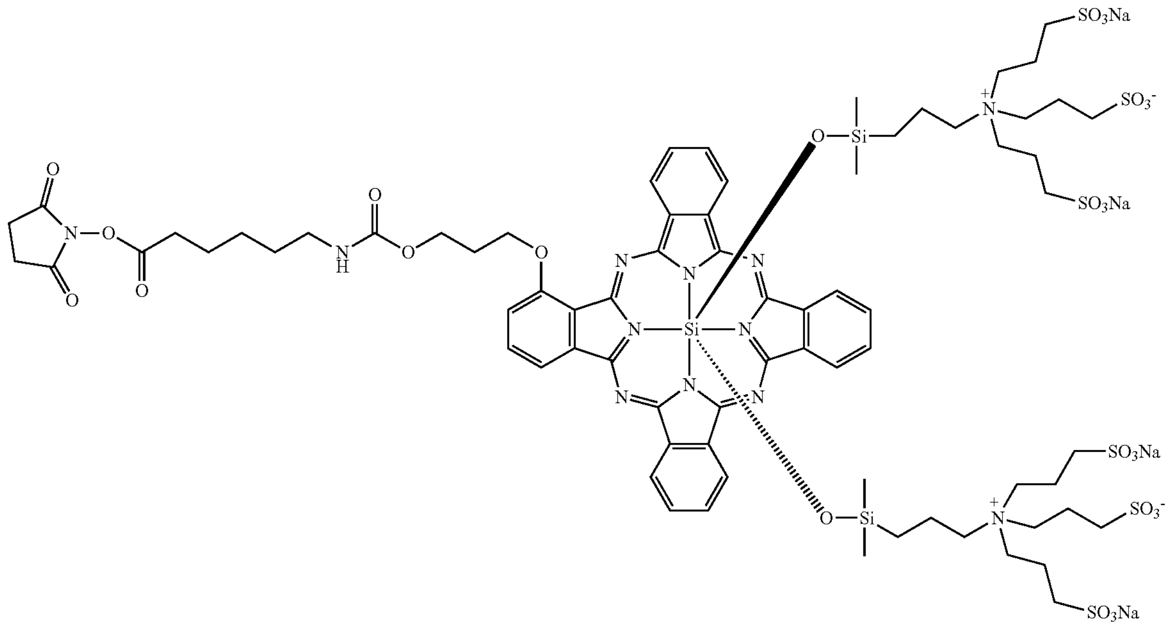

5. The conjugate according to claim 1, wherein the magnetic particle contains iron oxide or a gadolinium compound.

6. The conjugate according to claim 1, wherein the semiconductor particle is a quantum dot.

7. The conjugate according to claim 1, wherein the average particle diameter of the particle is from 1 nm to 50 nm.

8. The conjugate according to claim 1, wherein the number of the antibody molecules linked to the particle is from 1 to 20 per the particle.

9. A composition for pharmaceutical composition for photoimmunotherapy (PIT), comprising the conjugate of claim 1.

10. The conjugate according to claim 1, wherein the conjugate is for use in treatment of a tumor by photoimmunotherapy.

11. The conjugate according to claim 10, wherein the conjugate is further for use in imaging of a tumor.

12. The composition according to claim 9, wherein the composition is for use in treatment of a tumor by photoimmunotherapy.

13. The composition according to claim 12, wherein the composition is further for use in imaging of a tumor.

14. A method of phototherapy in a patient having a tumor, the method comprising:

irradiating the patient with a light beam having a wavelength of from 500 nm to 900 nm, wherein the patient has been previously administered the conjugate of claim 1.

15. The method according to claim 14, wherein the tumor therapeutic agent is further used for imaging of a tumor.

16. A method of treating a tumor, comprising:

administering the conjugate of claim 1 to a patient having a tumor; and irradiating the patient with a light beam having a wavelength of from 500 nm to 900 nm.

17. The method according to claim 16, further comprising, before the step of irradiating the patient with the light beam, a step of imaging a tumor of the patient having administered thereto the conjugate or the composition.

* * * * *